(12) United States Patent
Zeiner et al.

(10) Patent No.: US 9,456,917 B2
(45) Date of Patent: Oct. 4, 2016

(54) ENDOSCOPIC TRANSORAL DUODENAL SLEEVE APPLIER

(71) Applicant: Ethicon Endo-Surgery, Inc., Cincinnati, OH (US)

(72) Inventors: Mark S. Zeiner, Mason, OH (US); Mark S. Ortiz, Milford, OH (US); David B. Griffith, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 96 days.

(21) Appl. No.: 14/011,962

(22) Filed: Aug. 28, 2013

(65) Prior Publication Data

US 2015/0065938 A1   Mar. 5, 2015

(51) Int. Cl.
*A61M 5/00*   (2006.01)
*A61F 5/00*   (2006.01)
*A61F 2/04*   (2013.01)

(52) U.S. Cl.
CPC ............ *A61F 5/0076* (2013.01); *A61F 5/0089* (2013.01); *A61F 2/04* (2013.01)

(58) Field of Classification Search
CPC ........ A61F 2/04; A61F 5/0076; A61F 5/0089
USPC ............................................................. 604/8
See application file for complete search history.

(56) References Cited

U.S. PATENT DOCUMENTS

| 3,583,391 A | 6/1971 | Cox et al. |
| 4,134,405 A | 1/1979 | Smith |
| 4,315,509 A | 2/1982 | Smit |
| 4,416,267 A | 11/1983 | Garren et al. |
| 4,479,497 A | 10/1984 | Fogarty et al. |
| 4,519,392 A | 5/1985 | Lingua |
| 4,607,618 A | 8/1986 | Angelchik |

(Continued)

FOREIGN PATENT DOCUMENTS

| DE | 112011102287 | 2/2013 |
| EP | 1708641 | 10/2006 |

(Continued)

OTHER PUBLICATIONS

EPO Search Report dated Oct. 1, 2008 for corresponding patent application, European Patent Application No. PCT/US07/773251.

(Continued)

*Primary Examiner* — Leslie Deak
(74) *Attorney, Agent, or Firm* — Frost Brown Todd LLC

(57) ABSTRACT

A duodenal sleeve assembly comprises a sleeve, an expandable sealing member, a tether, and an expandable anchor. The sleeve is secured to the sealing member. The tether couples the anchor with the sealing member. A deployment instrument comprises a shaft assembly, a first retention member, and a second retention member. The first retention member selectively secures the sealing member to the shaft assembly. The second retention member selectively secures the anchor to the shaft assembly. When the first retention member is released, the sealing member expands outwardly to seal the proximal end of the sleeve against the mucosa of the patient's duodenum. When the second retention member is released, the anchor expands outwardly within the stomach to anchor the sleeve assembly relative to the stomach. The tether traverses the pylorus. The sleeve isolates chyme from enzymes in the duodenum; and the mucosa of the duodenum from nutrients in the chyme.

20 Claims, 18 Drawing Sheets

(56) References Cited

U.S. PATENT DOCUMENTS

| | | |
|---|---|---|
| 4,719,916 A | 1/1988 | Ravo |
| 4,925,446 A | 5/1990 | Garay et al. |
| 4,946,440 A | 8/1990 | Hall |
| 5,129,915 A | 7/1992 | Cantenys |
| 5,382,231 A | 1/1995 | Shlain |
| 5,389,089 A | 2/1995 | Bauer et al. |
| 5,558,665 A | 9/1996 | Kieturakis |
| 5,624,381 A | 4/1997 | Kieturakis |
| 5,868,141 A | 2/1999 | Ellias |
| 6,113,611 A | 9/2000 | Allen et al. |
| 6,302,917 B1 | 10/2001 | Dua et al. |
| 6,368,340 B2 | 4/2002 | Malecki et al. |
| 6,558,400 B2 | 5/2003 | Deem et al. |
| 6,558,429 B2 | 5/2003 | Taylor |
| 6,656,194 B1 | 12/2003 | Gannoe et al. |
| 6,705,989 B2 | 3/2004 | Cuschieri et al. |
| 6,740,121 B2 | 5/2004 | Geitz |
| 6,746,460 B2 | 6/2004 | Gannoe et al. |
| 6,773,440 B2 | 8/2004 | Gannoe et al. |
| 6,981,978 B2 | 1/2006 | Gannoe |
| 6,994,715 B2 | 2/2006 | Gannoe et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,044,957 B2 | 5/2006 | Foerster et al. |
| 7,066,945 B2 | 6/2006 | Hashiba et al. |
| 7,083,629 B2 | 8/2006 | Welker et al. |
| 7,097,650 B2 | 8/2006 | Welker et al. |
| 7,112,058 B2 | 9/2006 | Felix |
| 7,121,283 B2 | 10/2006 | Stack et al. |
| 7,122,058 B2 | 10/2006 | Levine et al. |
| 7,175,638 B2 | 2/2007 | Gannone et al. |
| 7,211,094 B2 | 5/2007 | Gannone et al. |
| 7,211,114 B2 | 5/2007 | Bessler et |
| 7,214,233 B2 | 5/2007 | Gannoe et al. |
| 7,220,237 B2 | 5/2007 | Gannoe et al. |
| 7,229,428 B2 | 6/2007 | Gannoe et al. |
| 7,267,694 B2 | 9/2007 | Levine et al. |
| 7,288,064 B2 | 10/2007 | Boustani et al. |
| 7,288,099 B2 | 10/2007 | Deem et al. |
| 7,288,101 B2 | 10/2007 | Deem et al. |
| 7,306,614 B2 | 12/2007 | Weller et al. |
| 7,329,285 B2 | 2/2008 | Levine et al. |
| 7,347,875 B2 | 3/2008 | Levine et al. |
| 7,476,256 B2 | 1/2009 | Meade et al. |
| 7,503,922 B2 | 3/2009 | Deem et al. |
| 7,510,559 B2 | 3/2009 | Deem et al. |
| 7,608,114 B2 | 10/2009 | Levine et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,708,684 B2 | 5/2010 | Demarais et al. |
| 7,753,870 B2 | 7/2010 | Demarais et al. |
| 7,753,928 B2 | 7/2010 | de la Torre et al. |
| 7,757,924 B2 | 7/2010 | Gerbi et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,771,382 B2 | 8/2010 | Levine et al. |
| 7,789,848 B2 | 9/2010 | Gannoe et al. |
| 7,815,589 B2 | 10/2010 | Meade et al. |
| 7,815,591 B2 | 10/2010 | Levine et al. |
| 7,819,836 B2 | 10/2010 | Levine et al. |
| 7,837,643 B2 * | 11/2010 | Levine et al. .............. 604/8 |
| 7,837,669 B2 | 11/2010 | Dann et al. |
| 7,862,574 B2 | 1/2011 | Deem et al. |
| 7,909,838 B2 | 3/2011 | Deem et al. |
| 7,931,693 B2 | 4/2011 | Binmoeller |
| 7,935,073 B2 | 5/2011 | Levine et al. |
| 7,967,798 B2 | 6/2011 | Reydel et al. |
| 7,976,488 B2 | 7/2011 | Levine et al. |
| 7,981,163 B2 | 7/2011 | Meade et al. |
| 8,057,420 B2 | 11/2011 | Meade et al. |
| 8,096,966 B2 | 1/2012 | Levine et al. |
| 8,109,895 B2 | 2/2012 | Williams et al. |
| 8,137,301 B2 | 3/2012 | Levine et al. |
| 8,162,871 B2 | 4/2012 | Levine et al. |
| 8,303,669 B2 | 11/2012 | Meade et al. |
| 8,403,877 B2 | 3/2013 | Priplata et al. |
| 8,425,451 B2 | 4/2013 | Levine et al. |
| 8,475,401 B2 | 7/2013 | Priplata et al. |
| 8,486,153 B2 | 7/2013 | Levine et al. |
| 8,491,519 B2 | 7/2013 | Chin |
| 8,574,184 B2 | 11/2013 | Errico et al. |
| 8,591,452 B2 | 11/2013 | Priplata et al. |
| 8,628,583 B2 | 1/2014 | Meade et al. |
| 9,237,944 B2 | 1/2016 | Meade et al. |
| 2001/0018593 A1 | 8/2001 | Nguyen et al. |
| 2001/0044595 A1 | 11/2001 | Reydel et al. |
| 2002/0111641 A1 | 8/2002 | Peterson et al. |
| 2002/0188318 A1 | 12/2002 | Carley et al. |
| 2004/0092892 A1 | 5/2004 | Kagan et al. |
| 2004/0107004 A1 | 6/2004 | Levine et al. |
| 2004/0148034 A1 | 7/2004 | Kagan et al. |
| 2004/0220682 A1 | 11/2004 | Levine et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0085923 A1 | 4/2005 | Levine et al. |
| 2005/0125020 A1 | 6/2005 | Meade et al. |
| 2005/0125075 A1 | 6/2005 | Meade et al. |
| 2005/0277975 A1 | 12/2005 | Saadat et al. |
| 2006/0009858 A1 | 1/2006 | Levine et al. |
| 2006/0106288 A1 | 5/2006 | Roth et al. |
| 2006/0155311 A1 | 7/2006 | Hashiba et al. |
| 2006/0161187 A1 | 7/2006 | Levine et al. |
| 2006/0217757 A1 | 9/2006 | Horndeski |
| 2007/0005147 A1 | 1/2007 | Levine et al. |
| 2007/0185518 A1 | 8/2007 | Hassier, Jr. |
| 2007/0239284 A1 | 10/2007 | Skerven et al. |
| 2007/0250020 A1 | 10/2007 | Kim et al. |
| 2007/0276428 A1 | 11/2007 | Haller et al. |
| 2008/0058840 A1 | 3/2008 | Albrecht et al. |
| 2008/0167629 A1 | 7/2008 | Dann et al. |
| 2008/0187206 A1 | 8/2008 | Sendai et al. |
| 2008/0208357 A1 | 8/2008 | Melanson et al. |
| 2008/0234834 A1 | 9/2008 | Meade et al. |
| 2008/0255587 A1 | 10/2008 | Cully et al. |
| 2008/0255678 A1 | 10/2008 | Cully et al. |
| 2009/0240340 A1 | 9/2009 | Levine et al. |
| 2009/0248171 A1 | 10/2009 | Levine et al. |
| 2010/0256776 A1 | 10/2010 | Levine et al. |
| 2010/0298632 A1 | 11/2010 | Levine et al. |
| 2010/0305590 A1 | 12/2010 | Holmes et al. |
| 2010/0331756 A1 | 12/2010 | Meade et al. |
| 2011/0004146 A1 | 1/2011 | Priplata et al. |
| 2011/0004234 A1 | 1/2011 | Priplata et al. |
| 2011/0004236 A1 | 1/2011 | Priplata et al. |
| 2011/0046537 A1 | 2/2011 | Errico et al. |
| 2011/0245752 A1 | 10/2011 | Levine et al. |
| 2011/0257580 A1 | 10/2011 | Meade et al. |
| 2011/0276091 A1 | 11/2011 | Melanson et al. |
| 2011/0301523 A1 | 12/2011 | Levine et al. |
| 2012/0143348 A1 | 6/2012 | Voegele |
| 2012/0184967 A1 | 7/2012 | Levine et al. |
| 2012/0215152 A1 | 8/2012 | Levine et al. |
| 2013/0012862 A1 | 1/2013 | Meade et al. |
| 2013/0030350 A1 | 1/2013 | Albrecht et al. |
| 2013/0253410 A1 | 9/2013 | Levine et al. |
| 2014/0018719 A1 | 1/2014 | Chamorro, III |

FOREIGN PATENT DOCUMENTS

| | | |
|---|---|---|
| EP | 1610720 | 2/2009 |
| EP | 2080242 | 7/2009 |
| EP | 1610719 | 1/2010 |
| EP | 2139438 | 1/2010 |
| EP | 2280669 | 2/2011 |
| EP | 1768618 | 4/2011 |
| EP | 2382948 | 11/2011 |
| EP | 2103286 | 10/2012 |
| EP | 1850812 | 12/2012 |

(56) References Cited

FOREIGN PATENT DOCUMENTS

| | | |
|---|---|---|
| EP | 2394612 | 4/2013 |
| JP | 2010-502312 | 1/2010 |
| JP | 2010-104853 | 5/2010 |
| JP | 2010-269158 | 12/2010 |
| JP | 2011-251164 | 12/2011 |
| JP | 2012-152576 | 8/2012 |
| JP | 2013-090940 | 5/2013 |
| WO | 01/35832 | 5/2001 |
| WO | 2004/049982 | 6/2004 |
| WO | 2004/060169 | 7/2004 |
| WO | 2004/087014 | 10/2004 |
| WO | 2005/060869 | 7/2005 |
| WO | 2005/060882 | 7/2005 |
| WO | 2006/016894 | 2/2006 |
| WO | 2006/034062 | 3/2006 |
| WO | 2006/078781 | 7/2006 |
| WO | 2006/078927 | 7/2006 |
| WO | 2006/102012 | 9/2006 |
| WO | 2006/133311 | 12/2006 |
| WO | 2007/075978 | 7/2007 |
| WO | 2008/028108 | 3/2008 |
| WO | WO 2008/039800 | 4/2008 |
| WO | 2009/085107 | 7/2009 |
| WO | 2011/031981 | 3/2011 |
| WO | WO 2011/120047 | 9/2011 |
| WO | 2012/006146 | 1/2012 |
| WO | 2012/072133 | 6/2012 |
| WO | 2012/072134 | 6/2012 |
| WO | 2012/072136 | 6/2012 |
| WO | 2012/072137 | 6/2012 |
| WO | 2012/072138 | 6/2012 |
| WO | 2012/072662 | 6/2012 |
| WO | 2012/107079 | 8/2012 |
| WO | 2012/136249 | 10/2012 |
| WO | 2013/023675 | 2/2013 |
| WO | 2013/023676 | 2/2013 |
| WO | 2013/023679 | 2/2013 |
| WO | 2013/026473 | 2/2013 |
| WO | 2013/026474 | 2/2013 |
| WO | 2013/028837 | 2/2013 |
| WO | 2013/028841 | 2/2013 |
| WO | 2013/087092 | 6/2013 |
| WO | 2013/087093 | 6/2013 |
| WO | 2013/087095 | 6/2013 |
| WO | 2013/087096 | 6/2013 |
| WO | 2013/185830 | 12/2013 |
| WO | 2014/012041 | 1/2014 |

OTHER PUBLICATIONS

European Search Report dated Aug. 19, 2009; Application No. 09250720.1.
European Search Report dated Jan. 27, 2014; Application No. 07814611.5.
International Preliminary Report dated Mar. 3, 2009; International Application No. PCT/US2007/77351.
International Preliminary Report dated Jan. 5, 2011; International Application No. PCT/US2009/048609.
International Preliminary Report re: PCT/US2014/052085 dated Mar. 1, 2016.
International Search Report dated Oct. 1, 2008; International Application No. PCT/US2007/77351.
International Search Report dated Dec. 30, 2009, International Application No. PCT/US2009/048609.
International Search Report and Written Opinion dated Nov. 12, 2014 for Application No. PCT/US2014/052085.
Supplementary Partial European Search Report re: 07814611 dated Jan. 14, 2014.

* cited by examiner

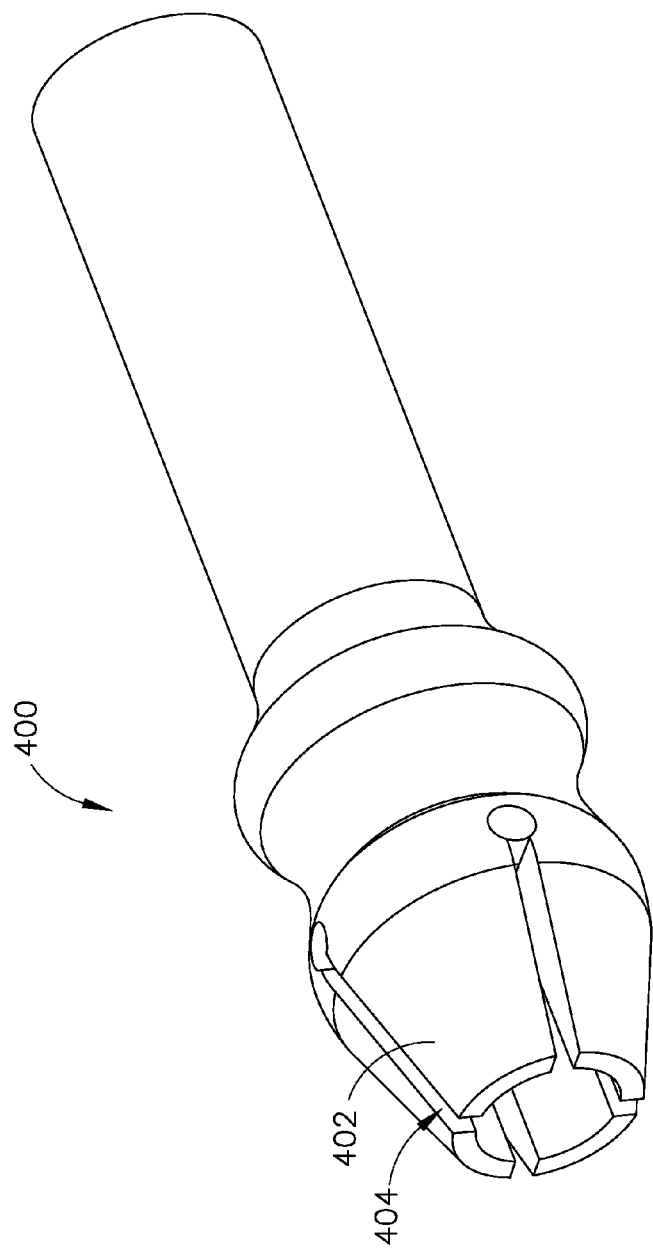

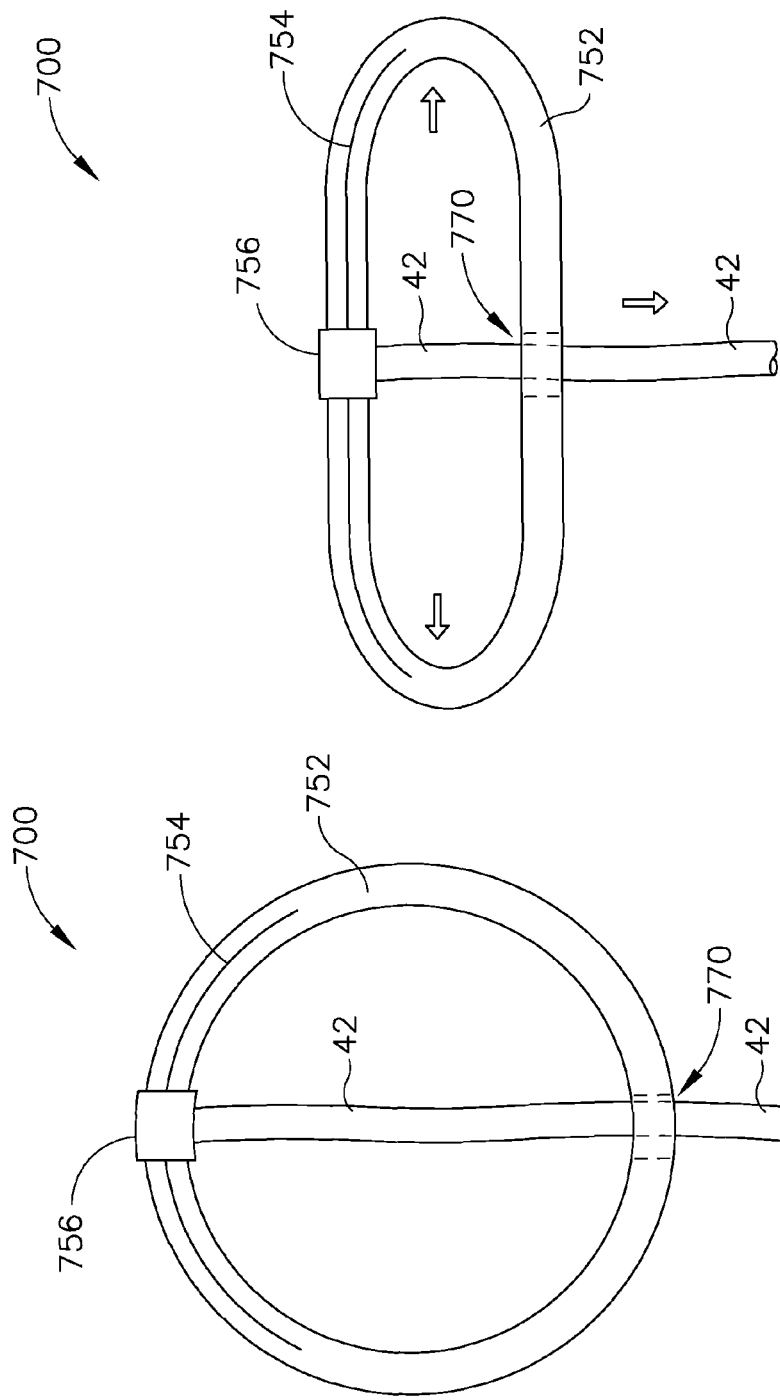

ENDOSCOPIC TRANSORAL DUODENAL SLEEVE APPLIER

BACKGROUND

In some instances, it may be desirable to deploy an endoluminal sleeve or other type of lining within a hollow body organ such as a stomach, intestine, etc. By way of example only, a sleeve may be positioned within a patient's duodenum to separate or bypass at least part of the food flow from the lined portions of the duodenum. In some patients, creating a physical barrier between ingested food and certain regions of the gastrointestinal wall by means of endoluminal sleeves may provide some degree of weight loss and/or treatment of type 2 diabetes. The presence of the barrier may influence or alter signaling (e.g., neural, endocrine, etc.) originating from the intestine and/or improve glycemic control. Contrary to traditional gastric bypass surgery, endoluminal sleeve surgery may be reversed and the sleeve may be removed after achievement of the desired clinical result.

An example of a duodenal sleeve is described in U.S. Pat. No. 7,267,694, entitled "Bariatric Sleeve," issued Sep. 11, 2007, the disclosure of which is incorporated by reference herein. The proximal end of a flexible, floppy sleeve of impermeable material defining a sleeve lumen is endoscopically deployed and anchored with the help of a barbed stent in the pylorus or in the superior section of the duodenum. The stent is also intended to ensure that the proximal lumen opening of the sleeve remains open. Chyme from the stomach enters the proximal lumen opening of the sleeve and passes through the sleeve lumen to the distal lumen opening. Digestive enzymes secreted in the duodenum pass through the duodenum on the outside of the sleeve, with the sleeve isolating the chyme from the enzymes. The enzymes and the chyme do not mix until the chyme exits from the distal lumen opening of the liner sleeve. In such a way, the efficiency of the process of digestion of the chyme may be diminished, reducing the ability of the gastrointestinal tract to absorb calories from the food. The sudden exposure of chyme to the small intestine (e.g., duodenum, proximal jejunenum, etc.) at the distal end of the barrier may lead to altered signaling from the gastrointestinal system resulting in an improved metabolic response.

Additional examples of endoluminal sleeves are disclosed in U.S. Pat. No. 7,121,283, entitled "Satiation Devices and Methods," issued Oct. 17, 2006, the disclosure of which is incorporated by reference herein; U.S. Pat. No. 7,037,344, entitled "Apparatus and Methods for Treatment of Morbid Obesity," issued May 2, 2006, the disclosure of which is incorporated by reference herein; U.S. Pub. No. 2008/0255678, entitled "Medical Apparatus and Method of Making the Same," published Oct. 16, 2008, the disclosure of which is incorporated by reference herein; and U.S. Pub. No. 2013/0030350, entitled "Devices and Methods for Anchoring an Endoluminal Sleeve in the GI Tract," published Jan. 31, 2013, the disclosure of which is incorporated by reference herein. Yet another example of an endoluminal sleeve is the EndoBarrier® by G.I. Dynamics, Inc. of Watertown, Mass.

While a variety of endoluminal sleeve devices and deploying instruments have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 11 depicts a perspective view of an exemplary alternative distal tip member for the instrument of FIG. 3;

FIG. 14A depicts another exemplary alternative anchor ring for the sleeve assembly of FIG. 1, in a non-compressed and non-splayed state; and FIG. 14B depicts the anchor ring of FIG. 14A in a splayed state.

Figure 1:
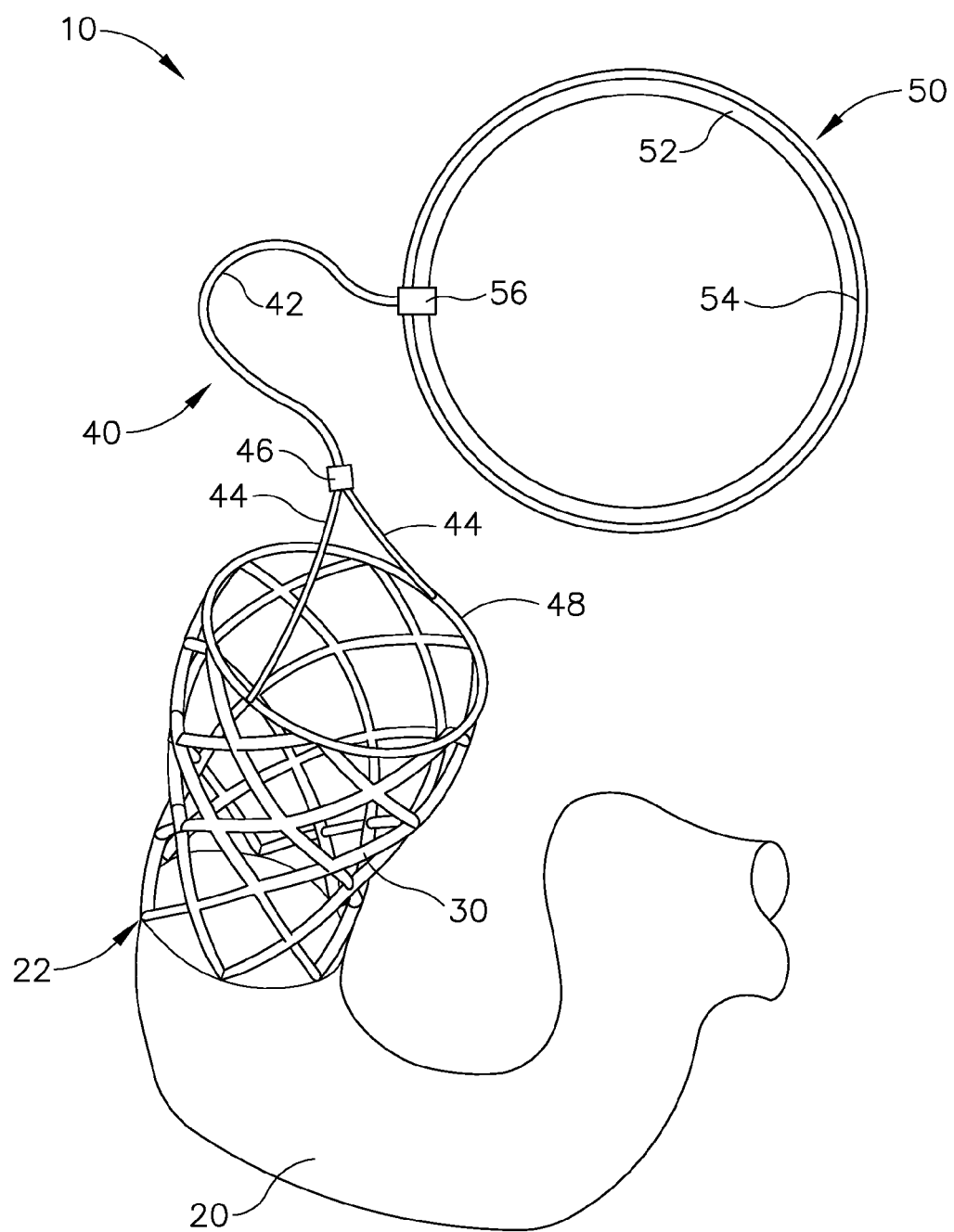
FIG. 1 depicts a perspective view of an exemplary duodenal sleeve assembly

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Duodenal Sleeve Assembly

FIG. 1 shows an exemplary duodenal sleeve assembly (10). Assembly (10) of this example comprises a duodenal sleeve (20), a sealing member (30), a tether assembly (40), and an anchor (50). Sleeve (20) of the present example comprises a flexible, non-permeable material (e.g., fluorinated ethylene propylene, etc.) that is configured to line at least part of the length of the duodenum (62), as will be described in greater detail below with reference to FIG. 2. It should also be understood that sleeve (20) may be selectively permeable such that sleeve (20) allows the flow of certain substances across the barrier that is provided by sleeve (20). Furthermore, sleeve (20) may be constructed in accordance with at least some of the teachings of U.S. Pat. Nos. 7,267,694; 7,121,283; 7,037,344; U.S. Pub. No. 2008/0255678; and/or U.S. Pub. No. 2013/0030350, the disclosures of all of which are incorporated by reference herein. In some instances, sleeve (20) is formed of a material that is at least partially biodegradable or bioabsorbable. By way of example only, the entire length of sleeve (20) may be bioabsorbable such that the entire sleeve (20) is absorbed after an appreciable period of time has passed. As another merely illustrative example, sleeve (20) may be formed as a series of non-absorbable segments that are joined by bioabsorbable elements. In such versions, the segments may separate from each other after an appreciable period of time has passed, and the segments may then pass through the patient's gastrointestinal tract. It should also be understood that sleeve (20) may have radiopaque stripes and/or other radiopaque markings along its length, to facilitate visualization of sleeve (20) under fluoroscopy.

Sealing member (30) is secured to the proximal end of sleeve (20). Sealing member (30) of the present example is in the form of a metallic woven stent that is coaxially aligned with the proximal end of sleeve (20) and is resiliently biased to expand outwardly. Sealing member (30) may nevertheless collapse to a reduced diameter configuration, such as to facilitate passage of sealing member (30) through a patient's pylorus (64) as will be described in greater detail below. In some versions, sealing member (30) comprises nitinol or spring steel, though it should be understood that any other suitable material or combination of materials may be used, including but not limited to elastomeric materials. In versions where sealing member (30) comprises nitinol or some other metallic material, the nitinol or other metallic material may be encased in a plastic membrane or elastomeric material; and/or otherwise be combined with some other material to form sealing member (30). In versions where sealing member (30) is formed of an elastomeric material (e.g., a plastic, etc.), sealing member (30) may take the form of a cylindraceous member with a repeating pattern of openings (e.g., diamond shaped openings, etc.) formed thereby to provide a stent like structure. Other suitable ways in which an elastomeric version of sealing member (30) may be formed will be apparent to those of ordinary skill in the art in view of the teachings herein. It should also be understood that sealing member (30) may take a variety of forms, including but not limited to a malleable stent, a resilient ring (e.g., in the form of a hyperbolic parabaloid, etc.), an expandable cuff, and/or various other kinds of structures.

Sealing member is configured to maintain the proximal end of sleeve (20) in an open configuration; and to further press against the mucosa of the proximal end of the duodenum (62) to seal sleeve (20) against the mucosa of the duodenum (62) as will be described in greater detail below. Also in the present example, sleeve (20) includes a reinforced region (22) at sealing member (30). In some versions, reinforced region (22) is formed by a layer of sleeve (20) positioned within the interior region of sealing member (30), wrapping over the proximal end of sealing member (30), and extending further over the exterior region of sealing member (30) to a point distal to the distal end of sealing member (30). Sleeve (20) may thus form two layers along the length of sealing member (30) and just distal to the distal end of sealing member (30). In some such versions, the layers of sleeve (20) are heat-sealed together in apposition. In some other versions, sleeve (20) is only secured to the interior region of sealing member (30) or only the exterior region of sealing member (30). Other suitable ways in which sleeve (20) may be secured and/or reinforced relative to sealing member (30) will be apparent to those of ordinary skill in the art in view of the teachings herein.

Tether assembly (40) couples the assembly of sleeve (20) and sealing member (30) with anchor (50). Tether assembly (40) of the present example comprises a primary tether (42) and a plurality of sub-tethers (44). Sub-tethers (44) are securably joined with primary tether (42) at a coupling (46); while primary tether (42) is securably joined with anchor (50) at another coupling (56). In some versions, the ends of sub-tethers (44) that are opposite to coupling (46) are secured directly to sealing member (30). In the present example, the ends of sub-tethers (44) that are opposite to coupling (46) are secured to sealing member (30) by a flexible tether ring (48). Ring (48) may be interwoven through sealing member (30) and/or may be wrapped within the proximal portion of sleeve (20). In some versions, ring (48) is in the form of a hyperbolic parabaloid. Ring (48) may be formed of silicone and/or any other suitable material(s). In some versions, sleeve (20) is wrapped about ring (48), and ring (48) is secured to sealing member (30) (e.g., by sutures, etc.) to thereby secure sleeve (20) to sealing member (30).

Other suitable ways in which tether assembly (40) may be coupled with the assembly of sleeve (20) and sealing member (30) will be apparent to those of ordinary skill in the art in view of the teachings herein. By way of example only, tether assembly (40) may be secured to the distal end of sealing member (30) and/or anywhere else along the length of sealing member (30) in addition to or in lieu of being secured to the proximal end of sealing member (30) as described above. For instance, sub-tethers (44) may be secured directly to the distal end of sealing member (30); or sub-tethers (44) may be secured to a ring (48) that is secured at the distal end of sealing member (30). In instances where tether assembly (40) is secured to the distal end of sealing member (30), sealing member (30) may become inverted when tether assembly (40) is pulled proximally to remove sleeve assembly (10) from the patient. In addition, while only two sub-tethers (44) are shown, it should be understood that any other suitable number of sub-tethers (44) may be used.

Tether (42) and sub-tethers (44) may be formed of any suitable flexible material(s), including but not limited to various kinds of plastics and/or metals, etc. Tether (42) and sub-tethers (44) may also have a variety of configurations. For instance, tether (42) and/or sub-tethers (44) may be the form of a braided cable or a monofilament. Tether (42) and/or sub-tethers (44) may also be covered in a protective coating such as silicone. In some versions, tether (42) and/or sub-tethers (44) comprise a radiopaque filament (e.g., silver, etc.) and/or some other form of wire embedded in silicone. As another merely illustrative example, tether (42) and/or sub-tethers (44) may include a radiopaque paste or other kind of radiopaque element, such as silver, platinum, iron, or a similar powder mixed with silicone. Including a radiopaque feature may enable visualization of tether assembly (40) under fluoroscopy. Tether (42) and sub-tethers (44) may also have a diameter between approximately 0.020 inches and approximately 0.300 inches. In some versions, tethers (42) and sub-tethers (44) have a diameter of approximately 0.085 inches, which enables tethers (42) and sub-tethers (44) to readily and innocuously pass through the pylorus (64). Various suitable materials and alternative configurations for tether assembly (40) will be apparent to those of ordinary skill in the art in view of the teachings herein.

Anchor (50) of the present example comprises a ring formed by an elastomeric member (52) encasing a resilient member (54). By way of example only, elastomeric member (52) may be formed of silicone and/or some other elastomeric material(s); while resilient member (54) may be formed of nitinol, spring steel, and/or some other resilient material(s). In some versions, elastomeric member (52) is omitted, such that anchor (50) is simply formed by resilient member (54). Elastomeric member (52) and resilient member (54) each define a complete ring in this example, though it should be understood that various other configurations may be used (e.g., a C-shape, etc.). In some versions, resilient member (54) comprises a wire or strip with its free ends joined together with a crimp or other pressure based connection. In some other versions, resilient member (54) does not define a complete ring. For instance, resilient member (54) may comprise a wire or strip that defines a segment of a ring, while elastomeric member (52) still defines a complete ring. In some such versions, coupling (56) is located at an approximate mid-point along the length of resilient member (54).

It should also be understood that anchor (50) may include one or more reinforcement features and/or stiffening features in the region at and near coupling (56) and/or in other regions. Such stiffening features may further prevent anchor (50) from passing through the pylorus (64) after sleeve assembly (10) is deployed. In some instances, stiffening is provided by increasing the cross-section of anchor (50) (e.g., by increasing the cross-section of resilient member (54)); or by adding segments of wire to anchor (50). Such increases in cross-section may be tapered to avoid an abrupt reduction in stiffness at any given point along the circumference of anchor (50). It should be understood that providing variation in the flexibility and stiffness along the circumference of anchor (50) may enable anchor (50) to more readily absorb peristaltic movement of the stomach (50); while still preventing anchor (50) from passing through the pylorus (64). Varying the flexibility and stiffness along the circumference of anchor (50) may further facilitate compressive installation of anchor (50) on deployment instrument (100) as will be described in greater detail below.

Like tether assembly (40), anchor (50) may include one or more radiopaque elements. For instance, elastomeric member (52) may include a radiopaque paste or other kind of radiopaque element, such as silver, platinum, iron, or a similar powder mixed with silicone. Including a radiopaque feature may enable visualization of anchor (50) under fluoroscopy. Various suitable materials and alternative configurations for anchor (50) will be apparent to those of ordinary skill in the art in view of the teachings herein.

Figure 2:
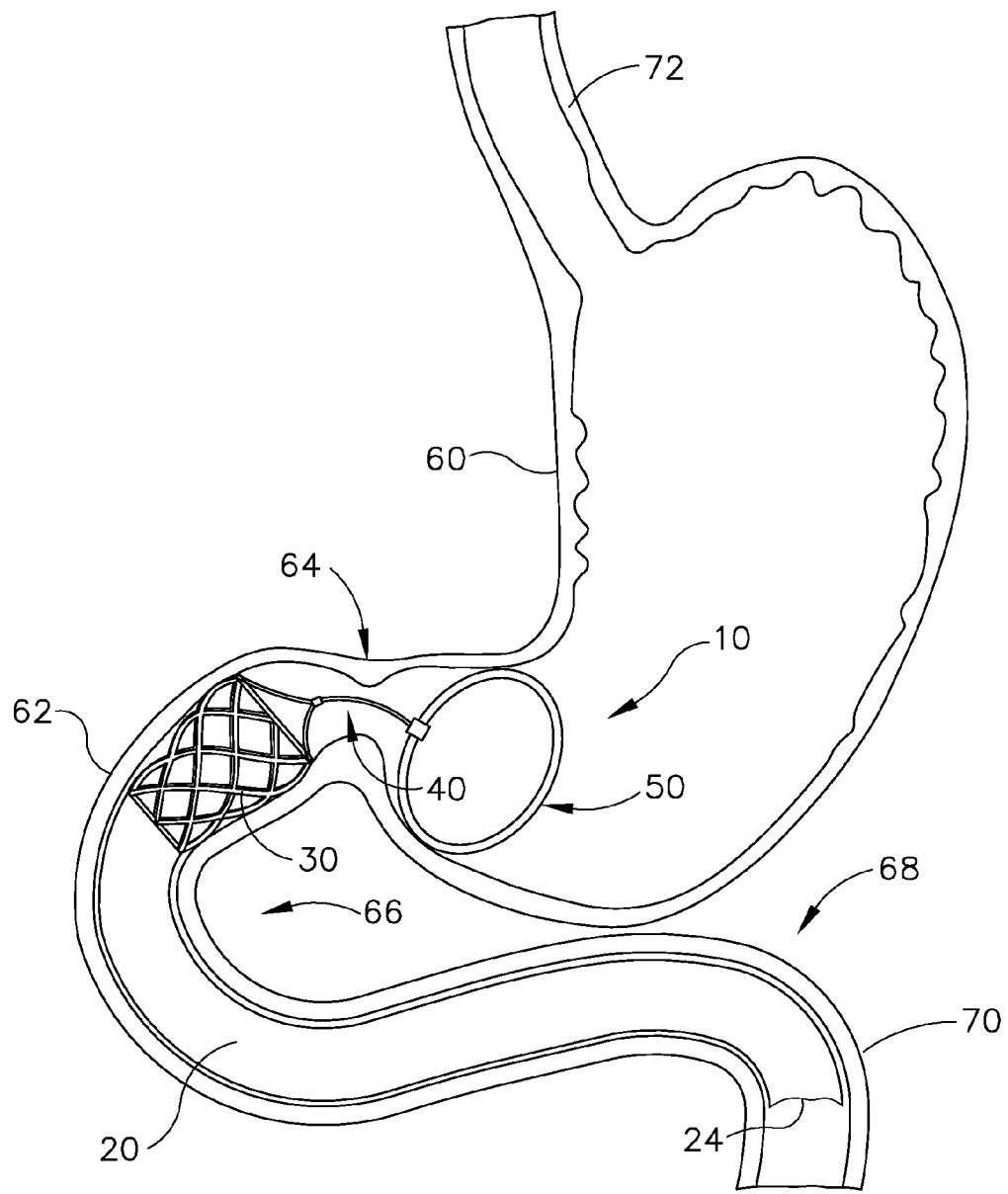
FIG. 2 depicts a diagrammatic view of the duodenal sleeve assembly of FIG. 1 deployed in a patient's stomach and duodenum.

Resilient member (54) is configured to bias anchor (50) to an expanded configuration as shown in FIGS. 1-2, where anchor (50) has an annular shape. However, it should be understood that resilient member (54) may be compressed such that anchor (50) forms an elongate, non-annular shape as will be described in greater detail below. When anchor (50) is in a compressed configuration, anchor (50) is configured to readily pass through a patient's esophagus (72). When anchor (50) is in the expanded configuration, anchor (50) is configured to remain in the stomach (60) without passing through the pylorus (64). Anchor (50) thus provides a particular balance of flexibility and rigidity. By way of example only, anchor (50) may have a cross section ranging from approximately 0.020 inches to approximately 0.300 inches. In some versions, anchor (50) has a cross section of approximately 0.156 inches. By way of further example only, the diameter of anchor (50) in the expanded state may be between approximately 25 mm and approximately 300 mm. In some versions, anchor (50) has a diameter of approximately 85 mm in the expanded state. Other suitable sizes and configurations that may be used for anchor (50) will be apparent to those of ordinary skill in the art in view of the teachings herein.

FIG. 2 shows assembly (10) positioned in a patient's stomach (60) and duodenum (62). It should be understood that the stomach (60) and the duodenum (62) may represent a stomach and duodenum of a patient with morbid obesity and/or type 2 diabetes. The pylorus (64) defines a restriction between the stomach (60) and the duodenum (62) and thereby serves as a gateway from the stomach (60) to the duodenum (62). The duodenum (62) includes a region known as the ampulla of Vater (66). Further downstream, the duodenojejunal flexure (68) leads to the jejunum (70).

As shown in FIG. 2, sleeve (20) is dimensioned to complement the inner diameter of the duodenum (62). While the flexible material forming sleeve (20) is configured to fit the contours of duodenum (62), the material is also sufficiently durable such that sleeve (20) may withstand the forces of peristalsis in the duodenum (62). In some versions, sleeve (20) has a length selected such that sleeve (20) runs along at least the entire length of the duodenum (62). In some other versions, sleeve (20) is shorter than the length of the duodenum (62). In the present example as shown in FIG. 2, the distal end (24) of sleeve (20) terminates at the duodenojejunal flexure (68). The material forming sleeve (20) is configured to withstand bile, enzymes in the duodenum (62), hydrochloric acid from the stomach (60), other chemicals/materials in the chyme passing from the stomach (60), etc. With sleeve (20) lining the mucosa of the duodenum (62), chyme passes from the stomach (60) into the interior of sleeve (20), and sleeve (20) isolates this chyme from enzymes, etc., that are excreted in the duodenum (62) until the chyme exits the distal end (24) of sleeve (20). Sleeve (20) further prevents the duodenum (62) from absorbing fat and other nutrients from chyme along the length of sleeve (20).

In the example shown in FIG. 2, sleeve assembly (10) is positioned such that the proximal end of sleeve (20) and sealing member (30) are located at just distal to the pylorus (64) and proximal to the ampulla of Vater (66), with the remainder of sleeve (20) extending along the rest of the length of the duodenum (62). Sealing member (30) is shown in the outwardly expanded configuration in FIG. 2, where sealing member (30) urges sleeve (20) radially outwardly and into contact with the mucosa of the duodenum (62). Sealing member (30) thus bears outwardly against sleeve (20) and the mucosa of the duodenum (62), thereby holding sleeve (20) in an open configuration. This resilient outward bearing by sealing member (30) also seals the proximal end of sleeve (20) against the mucosa of the duodenum (62) just distal to pylorus (64), thereby ensuring that chyme exiting the stomach (60) directly enters sleeve (20) from the pylorus (64). In other words, the sealing member (30) directs chyme from the stomach (60) into the lumen defined by sleeve (20). In some other versions, the proximal end of sleeve (20) and sealing member (30) are positioned in the stomach (60), just proximal to (upstream of) the pylorus (64). In still other versions, sealing member (30) may be configured to longitudinally span at least part of the pylorus (64).

Anchor (50) and tether assembly (40) cooperate to maintain the position of sleeve (20) in the duodenum (62). As shown, anchor (50) is in the expanded configuration, where anchor (50) defines an outer diameter that is greater than the inner diameter defined by the pylorus (64). Anchor (50) thus does not pass through pylorus (64); and instead engages the mucosa of the stomach (60). Tether assembly (40) traverses the pylorus (64) to join anchor (50) with the assembly of sleeve (20) and sealing member (30). While tether assembly (40) and anchor (50) are both flexible to some degree, tether assembly (40) and anchor (50) are configured to maintain the position of sleeve (20) in the duodenum (62) despite peristaltic forces acting against assembly (10). Tether assembly (40) and anchor (50) are also configured to withstand hydrochloric acid, etc. from the stomach (60).

II. Exemplary Duodenal Sleeve Deployment Instrument

Figure 3:
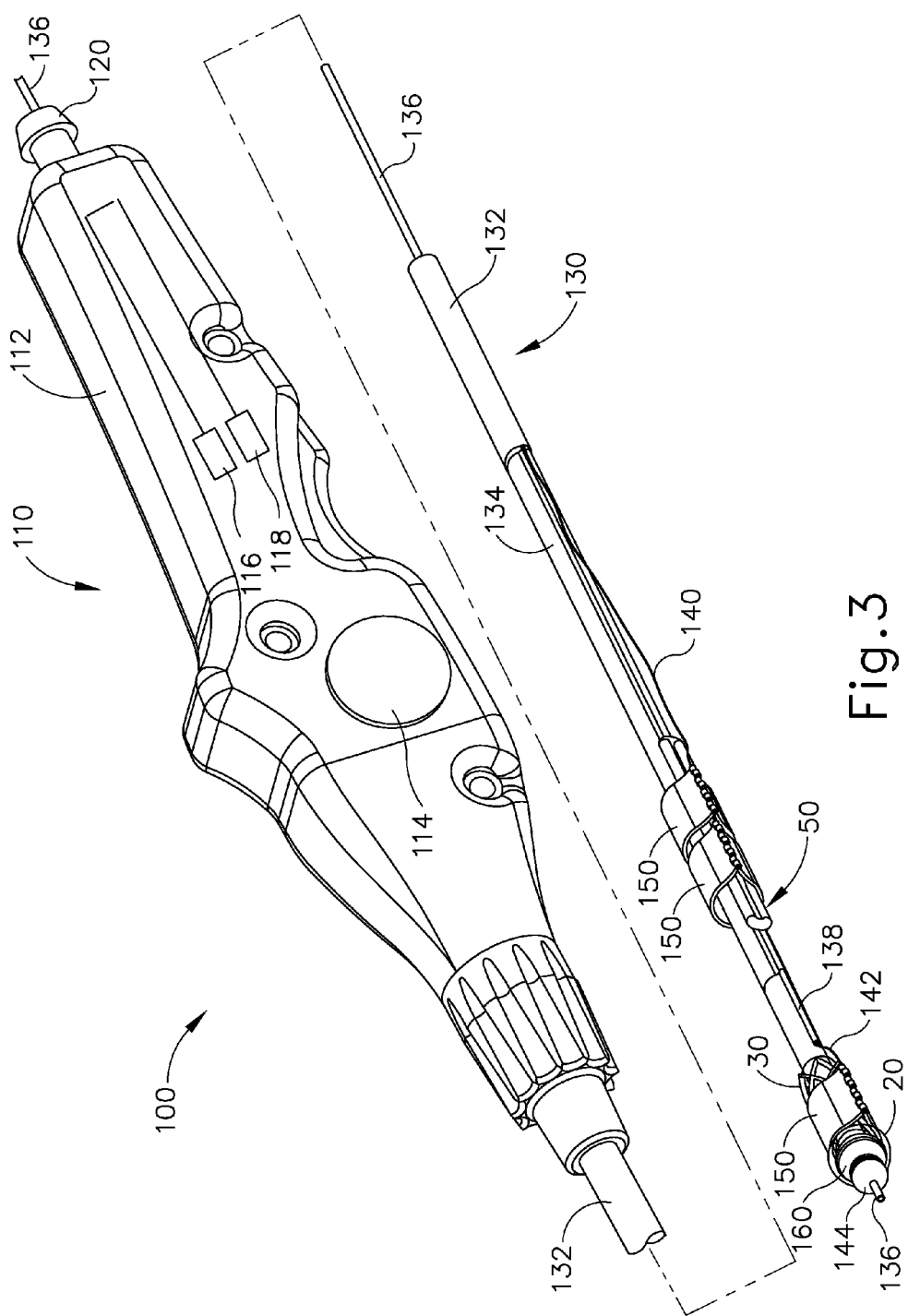
FIG. 3 depicts a perspective view of an exemplary deployment instrument coupled with the duodenal sleeve assembly of FIG. 1.

FIG. 3 shows an exemplary instrument (100) that may be used to transorally position and deploy (10) assembly in the duodenum (62) and stomach (60). Instrument (100) comprises a handle assembly (110) and a shaft assembly (130), which extends distally from handle assembly (110). In some versions, shaft assembly (130) is selectively coupled with handle assembly (110), such that handle assembly (110) may be re-sterilized and reused while shaft assembly (130) is disposed of after a single use. Handle assembly (110) comprises a housing (112), a deformable bulb (114), a first slider (116), a second slider (118), and a fluid port (120). Fluid port (120) may be coupled with a source of fluid (e.g., saline, etc.) via a conventional conduit to transmit fluid into handle assembly (110). Bulb (114) is operable to urge such fluid distally through shaft assembly (130) as will be described in greater detail below. Sliders (116, 118) are selectively and independently slidable proximally along housing (112) in order to retract deployment cables (140, 142) as will be described in greater detail below.

It should be understood that handle assembly (110) may be configured in numerous other ways. By way of example only, bulb (114) may be replaced or supplemented with a variety of other features that are operable to selectively cause fluid to be driven from handle assembly (110) to shaft assembly (130) (e.g., a piston assembly, a motorized pump, a valve in communication with a pressurized fluid source, etc.). Similarly, sliders (116, 118) may be replaced or supplemented with a variety of other features. In versions where sliders (116, 118) are used, handle assembly (110) may include a lockout feature that prevents slider (118) from sliding proximally until slider (116) has been slid to a proximal position. In some instances, both sliders (116, 118) may be locked out until guidewire tube (136) is pulled out of instrument (100) and/or until a fluid source is thereafter coupled with fluid port (120). As yet another variation, sliders (116, 118) may be consolidated into a single slider. Such a single slider may be operable to retract both deployment cables (140, 142); or both deployment cables (140, 142) may be consolidated into a single cable that is retracted by the single slider. Other suitable variations and operabilities for handle assembly (110) will be apparent to those of ordinary skill in the art in view of the teachings herein.

Shaft assembly (130) of the present example comprises an outer sheath (132), an inner tubular member (134), a guidewire tube (136), and a deployment cable shaft (138). Shaft assembly (130) is substantially flexible such that shaft assembly (130) may be inserted transorally through the esophagus (72) and stomach (60) to reach the duodenum (62) along a torturous path. However, shaft assembly (130) is generally kink-resistant and has enough column strength to enable the distal end of shaft assembly (130) to pass through the pylorus (64) without shaft assembly (130) significantly buckling in instances where the pylorus (64) presents an inner diameter that is smaller than the outer diameter of the distal end of shaft assembly (130). For instance, shaft assembly (130) may include a non-kinking material such as a metal coil that prevents shaft assembly (130) from undesirably buckling. By way of example only, such a metal coil may comprise extension spring part number 9664K48 from McMaster-Carr of Cleveland, Ohio. Such a metal coil may also have a varying pitch to selectively vary the flexibility of shaft assembly (130) along particular regions of the length of shaft assembly (130). It should also be understood that outer sheath (132) may have a varying durometer to provide varying flexibility along the length of shaft assembly (130). By way of example only, the proximal portion of shaft assembly (130) may be stiffer than the distal portion of shaft assembly (130), with the transition in stiffness being located somewhere between where anchor (50) is secured to shaft assembly (130) and where sealing member (130) is secured to shaft assembly (130).

Shaft assembly (130) of the present example has sufficient length to enable the distal end of shaft assembly (130) to reach the duodenum (62) transorally, with handle assembly (110) and a proximal portion of shaft assembly (130) remaining outside the patient while the distal end of shaft assembly (130) is positioned within the duodenum (62).

In some versions, shaft assembly (130) includes one or more radiopaque elements that promote visualization of the position of shaft assembly (130) within the patient under fluoroscopy. By way of example only, such a radiopaque element may comprise a metal coil, metal weave, metal wire, or radiopaque stripe that is incorporated in shaft assembly (130). As yet another merely illustrative variation, shaft assembly (130) may be filled with a barium solution (e.g., a diluted barium solution). Other suitable ways of promoting visualization of shaft assembly (130) under fluoroscopy or other imaging techniques will be apparent to those of ordinary skill in the art in view of the teachings herein.

Outer sheath (132) extends from handle assembly (110) along a substantial portion of the length of shaft assembly (130). The longitudinal position of outer sheath (132) is fixed relative to handle assembly (110). In the present example, outer sheath (132) distally terminates proximal to the longitudinal position where anchor (50) is loaded on shaft assembly (130). Of course, outer sheath (132) may distally terminate at any other suitable location; and the longitudinal position of outer sheath (132) relative to handle assembly (110) may be variable, if desired.

Sheath (132), inner tubular member (134), and guidewire tube (136) are coaxially arranged about a common axis in the present example; while deployment cable shaft (138) is offset from that common axis. In particular, deployment cable shaft (138) is laterally interposed between the exterior of inner tubular member (134) and the interior of outer sheath (132). In the present example, guidewire tube (136) exits handle assembly (110) via fluid port (120). Guidewire tube (136) must be fully withdrawn proximally from instrument (100) in order to enable a fluid conduit to be coupled with fluid port (120). This may prevent premature unfurling of sleeve (20) as will be described in greater detail below. Deployment cable (142) extends through deployment cable shaft (138) and is slidable within deployment cable shaft (138). Deployment cable (140) extends through a space defined between inner tubular member (134) and outer sheath (132) and is slidable through that space. In some versions, an additional deployment cable shaft (e.g., like deployment cable shaft (138)) is provided for deployment cable (140)).

Guidewire tube (136) is configured to slidably receive a guidewire (202), such that guidewire tube (136) and the remainder of instrument (100) may slide along guidewire (202) as will be described in greater detail below with reference to FIG. 8C. A ball tip (144) is removably secured to the distal end of guidewire tube (136) in the present example. Ball tip (144) is sized and configured to facilitate distal advancement of the distal end of shaft assembly (130) through the pylorus (64) as will be described in greater detail below. Ball tip (144) is also configured to be released from or otherwise break free from guidewire tube (136) after traversing the pylorus (64), such that ball tip (144) may subsequently pass through the patient's gastrointestinal tract and out with feces. By way of example only, ball tip (144) may be released by proximal retraction of either deployment cable (140, 142), which will be described in greater detail below.

Figure 4:
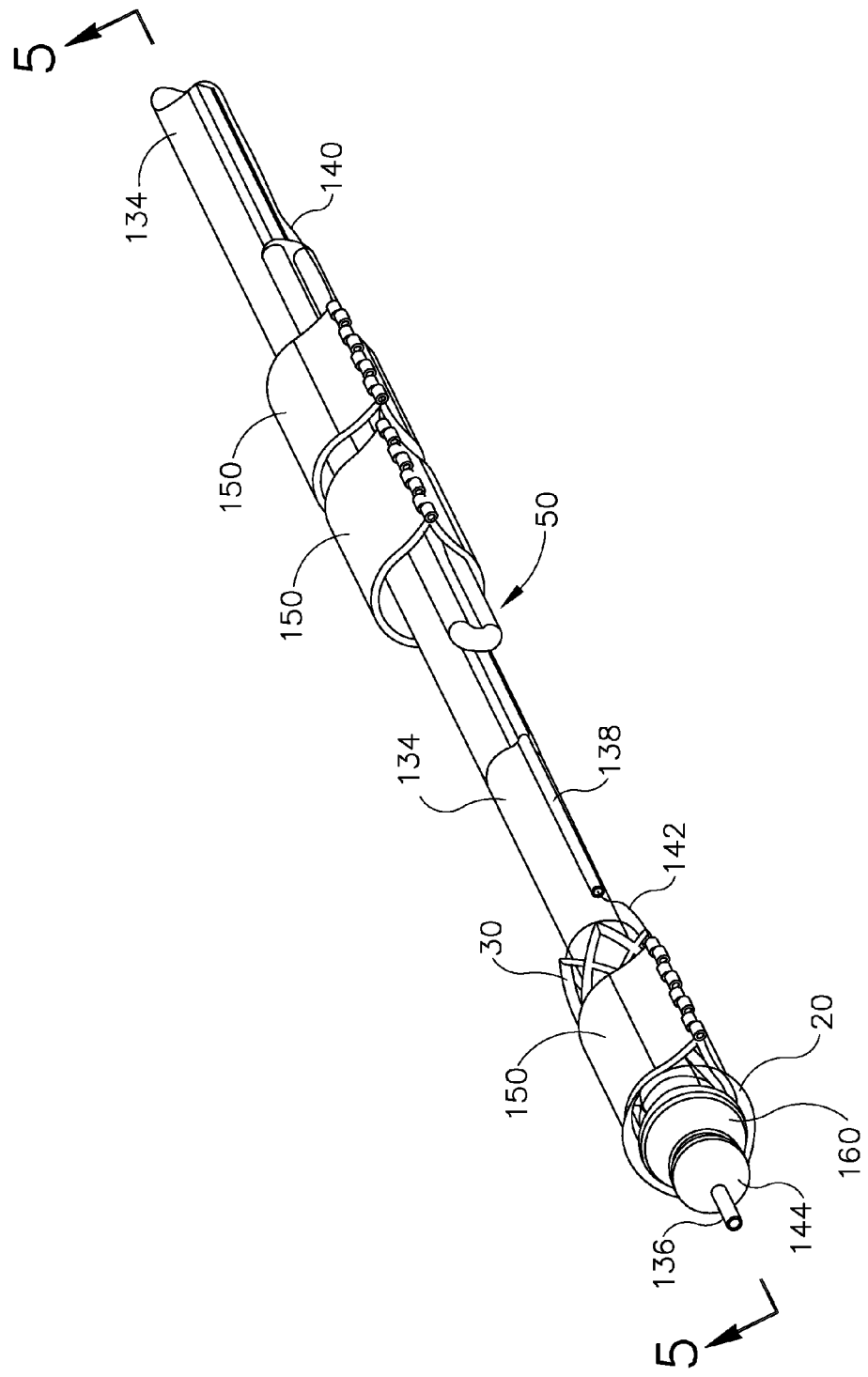
FIG. 4 depicts a partial perspective view of the distal end portion of the instrument of FIG. 3.
Figure 5:
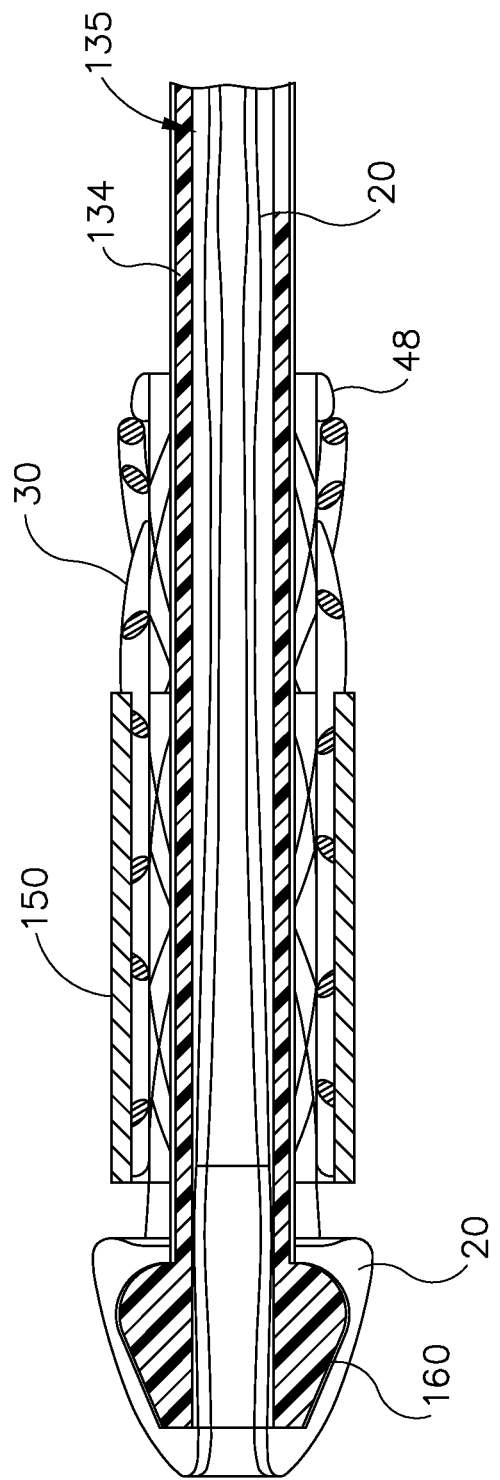
FIG. 5 depicts a cross-sectional view of the distal end portion of the instrument of FIG. 3, taken along line 5-5 of FIG. 4.
Figure 6:
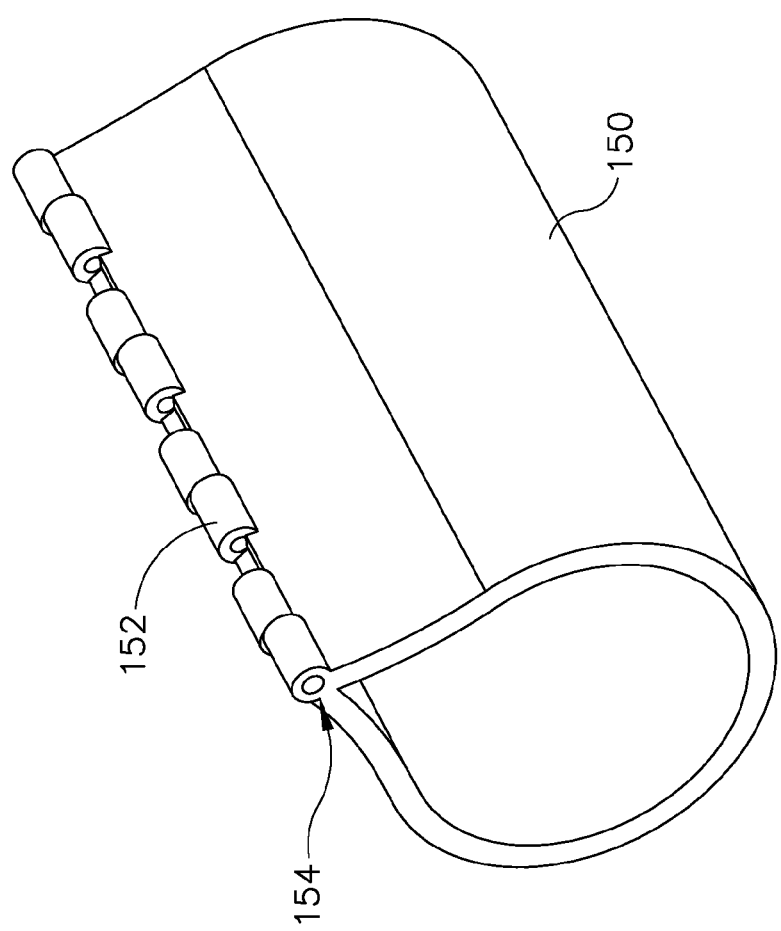
FIG. 6 depicts a perspective view of a retention cuff of the instrument of FIG. 3, in a closed configuration.
Figure 7:
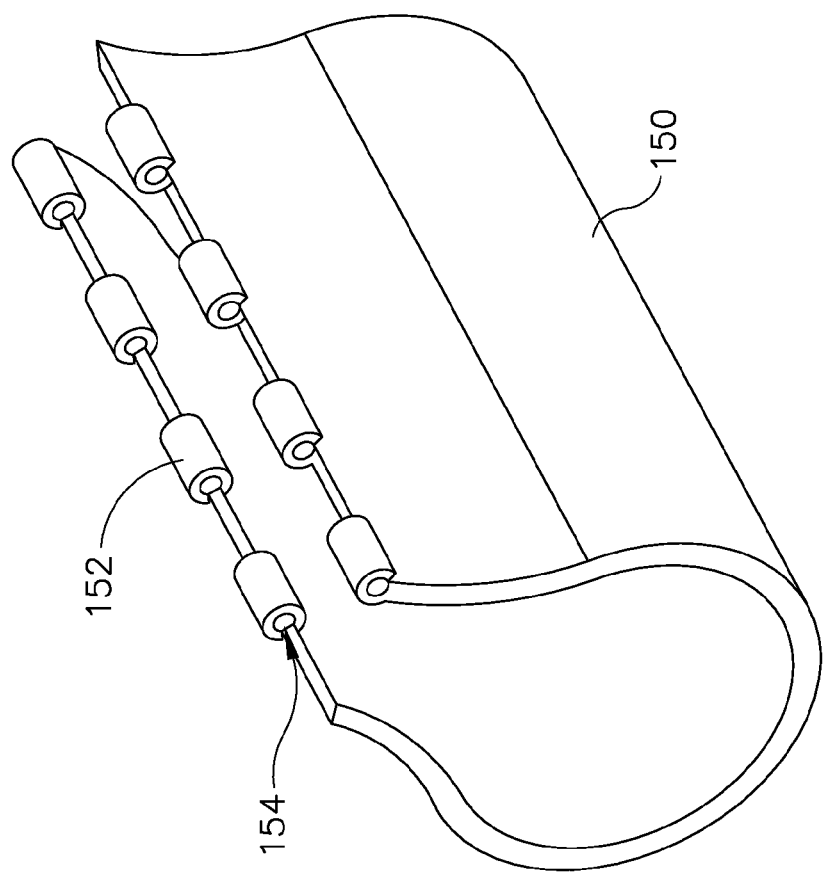
FIG. 7 depicts a perspective view of a retention cuff of the instrument of FIG. 3, in an open configuration.

As best seen in FIGS. 4-5, duodenal sleeve assembly (10) is releasably secured to the distal end of shaft assembly (130) by a set of retention members, such as retention cuffs (150). As best seen in FIGS. 6-7, each cuff (150) includes a series of knuckles (152) that define respective openings (154). Cuff (150) is resiliently biased to expand outwardly, as shown in FIG. 7, in a configuration where knuckles (152) are substantially separated. In some versions, the transverse distance separating the knuckles (152) along one longitudinal edge of cuff (150) and the knuckles (152) along the other longitudinal edge of cuff (150) is greater than the outer diameter of shaft assembly (130) when cuff is in the expanded configuration. Various suitable materials that may be used to form cuff (150) will be apparent to those of ordinary skill in the art in view of the teachings herein.

To secure duodenal sleeve assembly (10) to shaft assembly (130), cuffs (150) are deformed to a compressed state as shown in FIGS. 3-6. In this state, openings (154) of each knuckle (152) are aligned with each other, and deployment cables (140, 142) are fed through openings (154) to maintain cuffs (150) in the compressed state. As shown in FIG. 4, one cuff (150) is used to secure sealing member (30) to inner tubular member (134) while two cuffs (150) are used to secure anchor (50) to inner tubular member (134). The two cuffs (150) secured about anchor (50) share a common deployment cable (140); while the cuff secured about sealing member (30) has its own deployment cable (142). In some other versions, a single deployment cable (142) passes through all cuffs (150). In some such versions, the single deployment cable (142) may be withdrawn proximally through a first range of motion to release the distal-most cuff (150) from sealing member (30); then further proximally through a second range of motion to release the proximal-most cuffs (150) from anchor (50).

While a total of three cuffs (150) are used in the present example, it should be understood that any other suitable number of cuffs (150) may be used to secure sealing member (30) and anchor (50) to inner tubular member (134). It should be noted that tether assembly (40) is omitted from FIGS. 3-4 for the sake of clarity. It should also be noted that one or more additional cuffs (150) may be releasably secured about tether assembly (40), if desired. Regardless of whether any cuffs (150) are releasably secured about tether assembly (40), any cuffs (150) that are releasably secured to shaft assembly (130) may be coupled together by any suitable kind of tether(s). Having cuffs (150) so tethered together may facilitate transoral removal of cuffs (150) from the patient, if such removal is necessary. By way of example only, cuffs (150) may be tethered to one or both deployment cables (140, 142), such that cuffs (150) may be removed from the patient by retracting one or both deployment cables (140, 142) from the patient. Cuffs (150) may also be tethered to shaft assembly (130), such that cuffs (150) may be removed from the patient with shaft assembly (130). In some versions, cuffs (150) are formed of a biodegradable or bioabsorbable material, such that cuffs (150) do not need to be withdrawn from the patient.

As best seen in FIG. 5, sleeve (20) is captured between sealing member (30) and inner tubular member (134), passes around integral tip (160), and passes back through the lumen (135) defined by inner tubular member (134). Sleeve (20) is thus carried by shaft assembly (130) in an inverted configuration, with the distal end (24) of sleeve (20) being positioned proximally within inner tubular member (134). As will be described in greater detail below, sleeve (20) may transition from this inverted configuration and be expelled distally from lumen (135) of inner tubular member (134) by fluid communicated from handle assembly (110). While sleeve (20) is in the inverted configuration as shown in FIG. 5, guidewire tube (136) may extend through the interior defined by inverted sleeve (20). Guidewire tube (136) may thus protect inverted sleeve (20) from potential damage that might otherwise be caused by sliding instrument (100) along guidewire (202). Guidewire tube (136) and ball tip (144) are omitted from FIG. 5 for clarity. It should be understood that guidewire tube (136) may be removed from shaft assembly (130) before sleeve (20) is deployed as described in greater detail below, such that guidewire tube (136) will not inhibit deployment of sleeve (20).

As also best seen in FIG. 5, integral tip (160) of inner tubular member (134) has a frustoconical shape presenting a tapered profile. In addition to the shape of ball tip (144), the shape of integral tip (160) may facilitate passage of the distal end of shaft assembly (130) through the pylorus (64) as instrument (100) is used to deploy sleeve assembly (10). An example of such deployment will be described in greater detail below.

III. Exemplary Deployment of Duodenal Sleeve Using Deployment Instrument

Figure 8A:
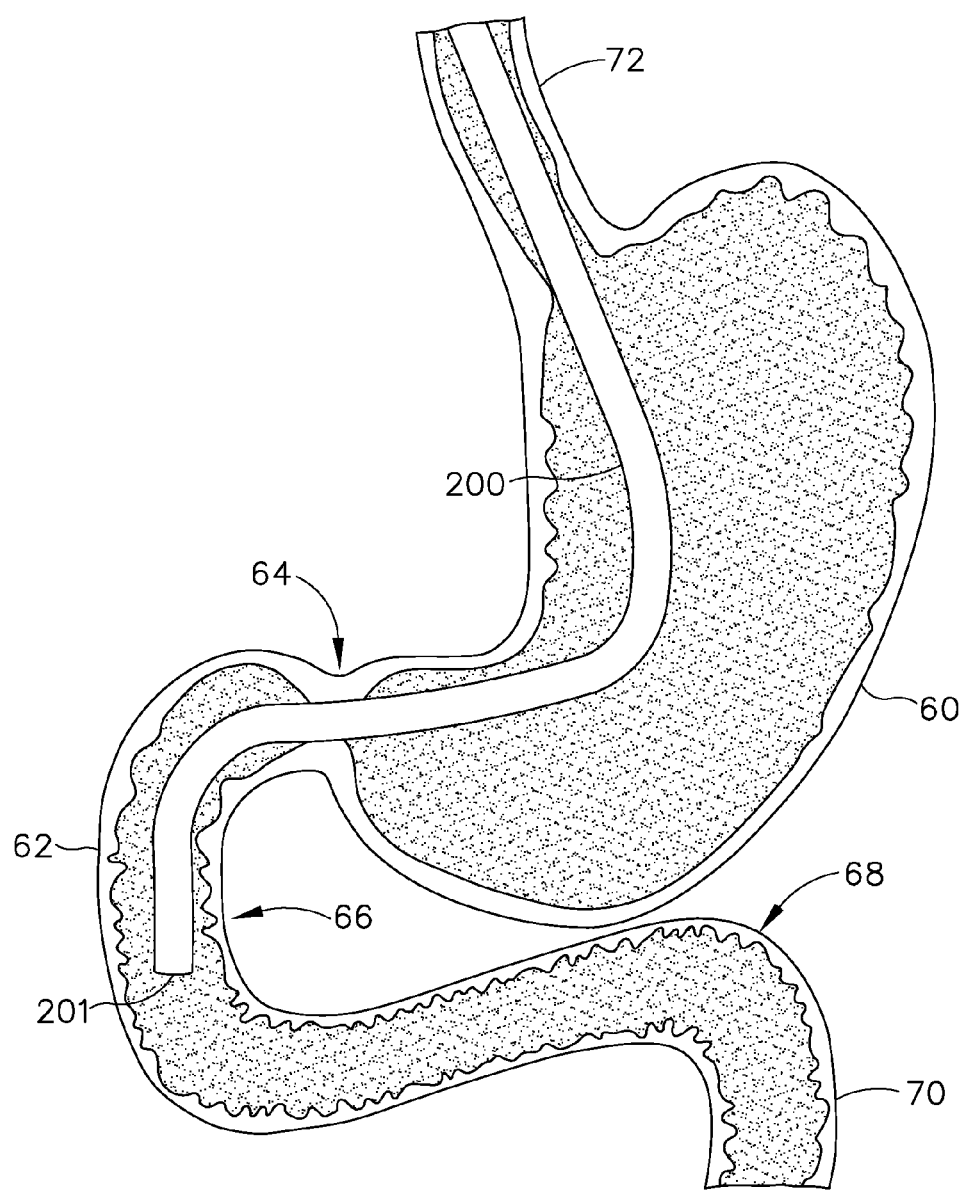
FIG. 8A depicts a diagrammatic view of an endoscope inserted transorally into a patient's duodenum via the esophagus and stomach.
Figure 8B:
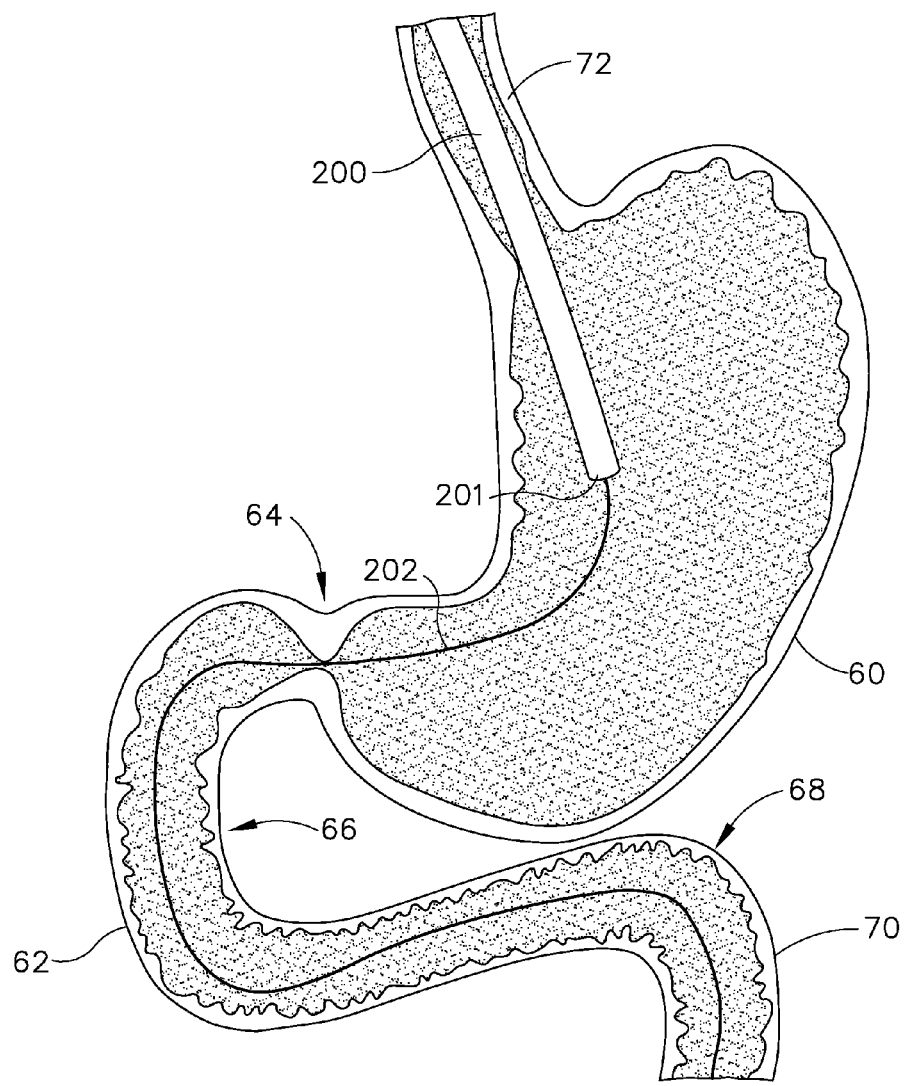
FIG. 8B depicts a diagrammatic view of the endoscope of FIG. 8A being withdrawn from the patient, leaving behind a guidewire in the patient's duodenum.
Figure 8C:
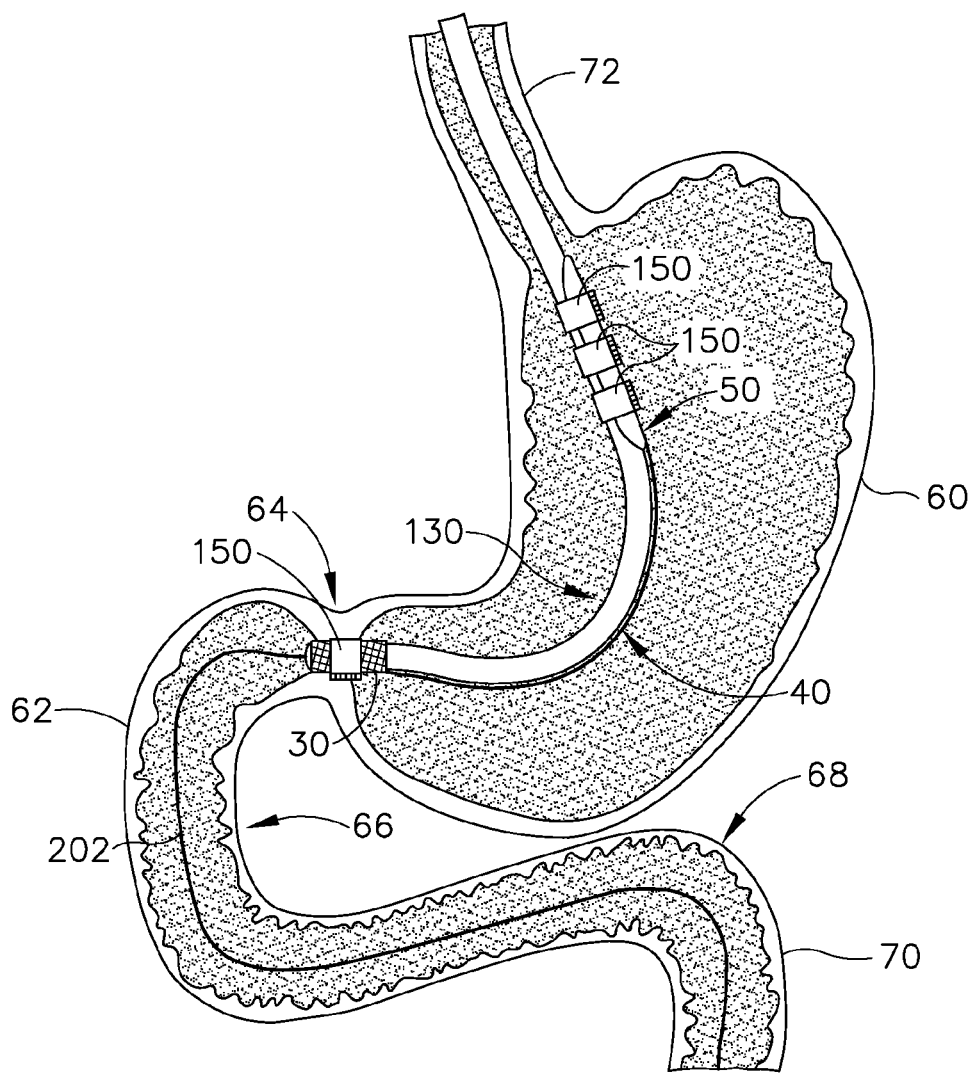
FIG. 8C depicts a diagrammatic view of the instrument of FIG. 3 being advanced distally along the guidewire of FIG. 8B, with the distal end of the instrument passing through the patient's pylorus.

FIGS. 8A-F show an exemplary method of deploying sleeve assembly (10). In particular, FIG. 8A shows a conventional steerable endoscope (200) inserted transorally through a patient's esophagus (72), through the stomach (60), and through the pylorus (64), such that the distal end (201) of endoscope (200) is located within the duodenum (62). The operator viewing the images captured by endoscope (200) may rely on visual confirmation that the distal end of endoscope (200) has reached the duodenum (62). Next, a conventional guidewire (202) is advanced distally through a working channel of endoscope (200), such that guidewire (202) is eventually positioned in the duodenum (62), and endoscope (200) is withdrawn from the duodenum (62) as shown in FIG. 8B.

Figure 8D:
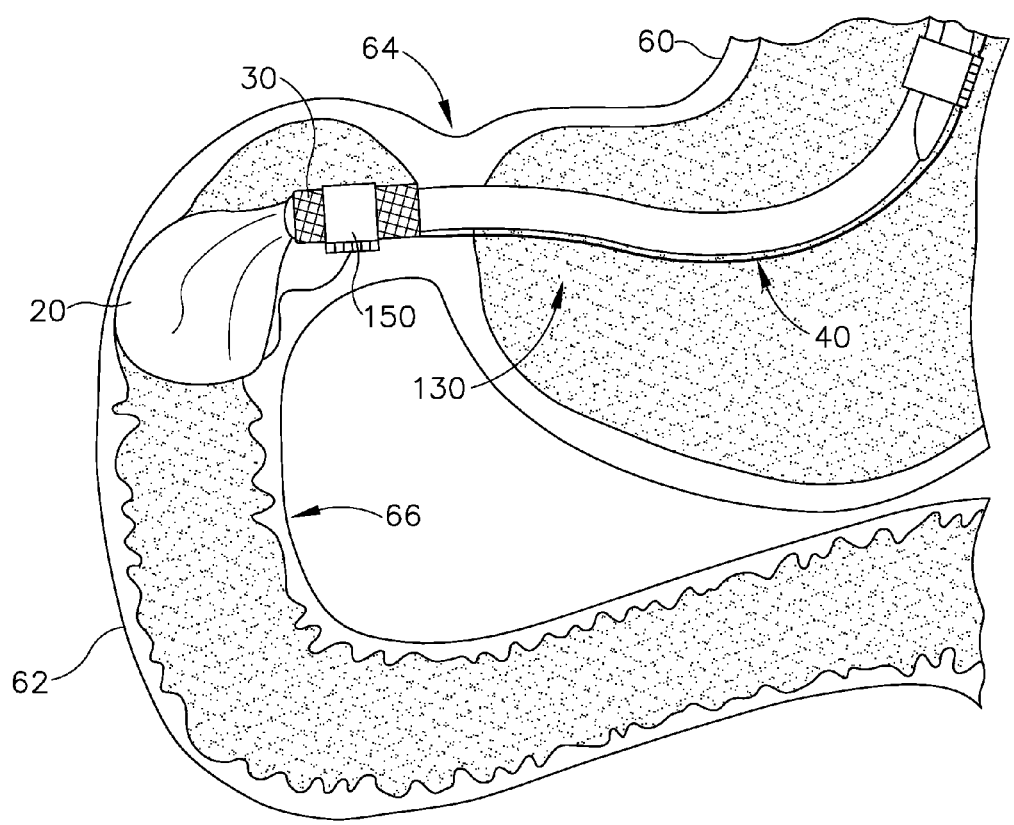
FIG. 8D depicts a diagrammatic view of the sleeve of the sleeve assembly of FIG. 1 being deployed from the instrument of FIG. 3 in the patient's duodenum.

Once endoscope (200) has been fully retracted from the patient and has been removed from guidewire (202), instrument (100) is slid along guidewire (202) with guidewire (202) positioned in the lumen of guidewire tube (136). Shaft assembly (130) follows along guidewire (202) such that the distal end of shaft assembly (130) eventually reaches the pylorus (64) as shown in FIG. 8C. Once the distal end of shaft assembly (130) reaches the pylorus (64), ball tip (144) and integral tip (160) assist in dilating the pylorus (64); and thereby provide a substantially smooth lead-in for features of shaft assembly (130) that are proximal to ball tip (144) and integral tip (160). Shaft assembly (130) continues to advance further distally such that sealing member (30) is positioned just distal to the pylorus (64) yet proximal to the ampulla of Vater (66), as shown in FIG. 8D. Ball tip (144) is released from shaft assembly (130); and guidewire tube (136) and guidewire (202) are also removed from shaft assembly (130).

With guidewire tube (136) being pulled completely out of fluid port (120), a fluid conduit is secured to fluid port (120) to couple handle assembly (110) with a fluid source. At this stage, bulb (114) is actuated to communicate fluid through shaft assembly (130) to begin unfurling sleeve (20) distally in the duodenum (64), as also shown in FIG. 8D. The distally flowing fluid may effectively close off the open distal end of sleeve (20) (which is initially positioned within inner tubular member (134) at this stage), such that the distally flowing fluid will push distally on the distal end of sleeve (20) to drive sleeve (20) distally out of the interior of inner tubular member (134). In some versions, the distal end of sleeve (20) may already be closed by an elastic band that encircles the distal end of sleeve (20). Such an elastic band may be resiliently biased to compress the distal end of sleeve (20), and may compress the distal end of sleeve against guidewire tube (136) when guidewire tube (136) is still positioned in sleeve (20). When guidewire tube (136) is pulled out of instrument (100), the elastic band may further compress, completing closure of the distal end of sleeve (20). In some other versions, a sticky biocompatible media such as honey, light biocompatible glue, grease, etc., is be used to temporarily seal the distal end of sleeve (20), in addition to or in lieu of an elastic band.

It should be understood that the distal-most cuff (150) may secure sealing member (30) and the proximal portion of sleeve (20) to inner tubular member (134) with enough force to provide a fluid-tight seal between sealing member (30), sleeve (20), and the exterior of inner tubular member (134). This may prevent fluid from leaking at the interface between sealing member (30) and inner tubular member (134), thereby ensuring that the liquid communicated distally through shaft assembly (130) properly unfurls sleeve (20). Once sleeve (20) reaches a distally unfurled state, the pressure of fluid within sleeve (20) will drive the sidewall of sleeve (20) outwardly to open the distal end of sleeve (20). In versions where the distal end of sleeve (20) is initially held closed with an elastic band, the pressure of fluid within sleeve (20) may drive the sidewall of sleeve (20) outwardly with sufficient force to push the elastic band distally off of the distal end of sleeve (20), thereby letting the distal end of sleeve (20) open. The elastic band may then simply pass through the patient's gastrointestinal tract.

Figure 8E:
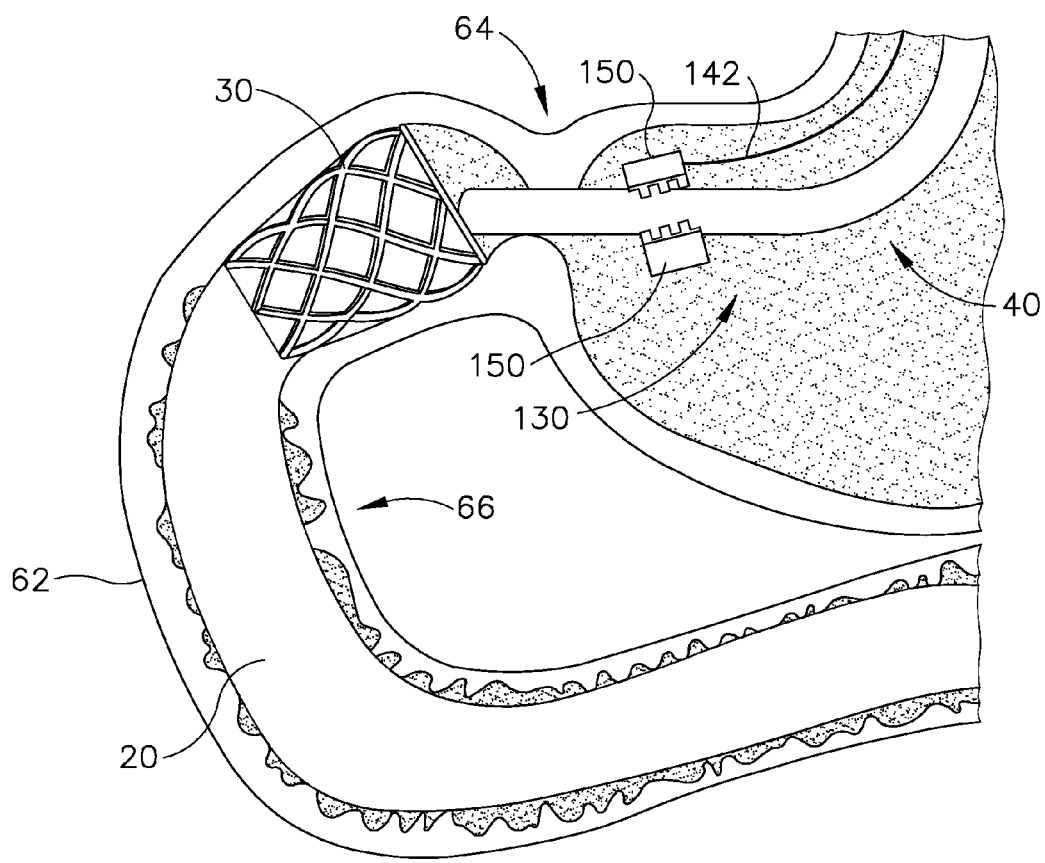
FIG. 8E depicts a diagrammatic view of the sleeve assembly of FIG. 1 deployed from the instrument of FIG. 3 in the patient's duodenum, with the sealing member of the sleeve assembly of FIG. 1 being released by a retention cuff of the instrument of FIG. 3.

After sleeve (20) has been fully unfurled distally in the duodenum (64), slider (118) is retracted proximally to pull deployment cable (142) proximally. Once deployment cable (142) is pulled from all of the knuckles (152) of the distal-most cuff (150), the distal-most cuff (150) resiliently expands outwardly to release sealing member (30) from shaft assembly (130). In some instances, as shown in FIG. 8E, the distal-most cuff (150) is also pulled proximally relative to shaft assembly (130) after the distal-most cuff (150) has been released from shaft assembly (130) and transitioned to the expanded state. Such proximal movement of the distal-most cuff (150) may provide additional clearance for sealing member (30) to freely expand. By way of example only, deployment cable (142) may be operable to pull the distal-most cuff (150) proximally relative to shaft assembly (130) after deployment cable (142) has released knuckles (152). Various suitable ways in which the distal-most cuff (150) may be pulled proximally relative to shaft assembly (130) after cuff (150) releases sealing member (30) will be apparent to those of ordinary skill in the art in view of the teachings herein.

Figure 8F:
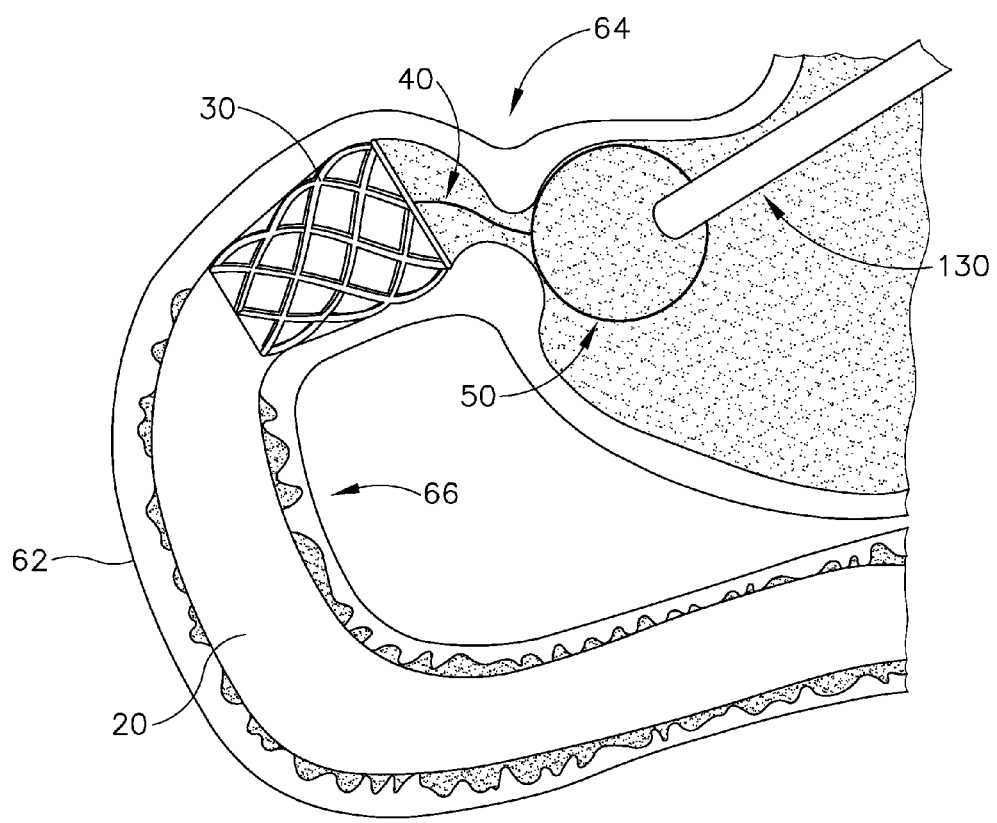
FIG. 8F depicts a diagrammatic view of the anchor ring of the sleeve assembly of FIG. 1 having been released by retention cuffs of the instrument of FIG. 3 in the patient's stomach.

In the present example, the resilience of sealing member (30) is alone sufficient to drive sealing member (30) outwardly to an expanded state, where sealing member (30) bears outwardly against the mucosa of the duodenum (62) and thereby seals the proximal end of sleeve (20) against the mucosa of the duodenum (62). In some other versions, shaft assembly (130) includes an inflatable member or otherwise expandable member that operable to drive sealing member (30) outwardly and thereby assist in transitioning sealing member (30) from the compressed state to the expanded state. After sealing member (30) has been transitioned to the expanded state as shown in FIG. 8E, shaft assembly (130) is withdrawn further proximally and slider (116) is retracted proximally to pull deployment cable (140) proximally. Once deployment cable (140) is pulled from the knuckles (152) of the cuffs (150) holding anchor (50) to shaft assembly (130), those cuffs (150) expand outwardly to release anchor (50) from shaft assembly (130). This release of cuffs (150) allows anchor (50) to resiliently expand to the expanded state as shown in FIG. 8F. Instrument (100) may then be fully withdrawn from the patient's stomach (60) and esophagus (72), leaving sleeve assembly (10) fully deployed as shown in FIG. 2 and described above. Other suitable ways in which sleeve assembly (10) may be deployed will be apparent to those of ordinary skill in the art in view of the teachings herein.

Once sleeve assembly (10) has been deployed in the patient, there are numerous ways in which a physician may determine whether sleeve assembly (10) is properly positioned and properly operating within the patient. By way of example only, the patient may be orally administered methylene blue or some other dye. This may affect the color of the patient's urine if the fluid properly travels through sleeve (20). In some instances, the fluid that is communicated through fluid port (120) to unfurl sleeve (20) comprises methylene blue or some other dye. As another merely illustrative example, fluoroscopy may be used to determine whether sleeve assembly (10) is properly positioned and properly operating within the patient. As noted above, sleeve (20) may include radiopaque stripes along its length. If these stripes show a non-continuous shape under fluoroscopy, it may indicate that the patency of sleeve (20) is compromised. For instance, if the stripes converge in a tight helix, it may indicate that sleeve (20) is twisted within the duodenum (64). If the stripes double back on themselves, it may indicate intussception of the duodenum (64) or the jejunum (70). If the stripes fold back on themselves, it may indicate a fold in sleeve (20). As yet another merely illustrative example, a pressure gauge may be used to check the patency of the deployed sleeve (20). Other suitable ways in which the proper positioning and operation of sleeve assembly (10) may be verified will be apparent to those of ordinary skill in the art in view of the teachings herein.

In the event that sleeve assembly (10) is to be removed, sealing member (30) may be compressed in order for sealing member (30) to clear the inner diameter of the pylorus (64) and esophagus (72) for proximal retraction. In versions where tether assembly (40) is secured to the distal end of sealing member (30), pulling proximally on tether assembly (40) may cause sealing member (30) to invert, and such inversion may facilitate proximal passage of sealing member (30) through the pylorus (64). Anchor (50) may also be compressed in order for anchor (50) to clear the inner diameter of the esophagus (72) for proximal retraction. Sleeve assembly (10) may thus be pulled from the patient transorally. Various suitable ways in which sleeve assembly (10) may be removed from the patient will be apparent to those of ordinary skill in the art in view of the teachings herein.

IV. Exemplary Variations of Duodenal Sleeve Deployment Instrument

As noted above, instrument (100) may be subject to various modifications. Some merely illustrative examples of such modifications are described below; while other examples will be apparent to those of ordinary skill in the art in view of the teachings herein.

Figure 9:
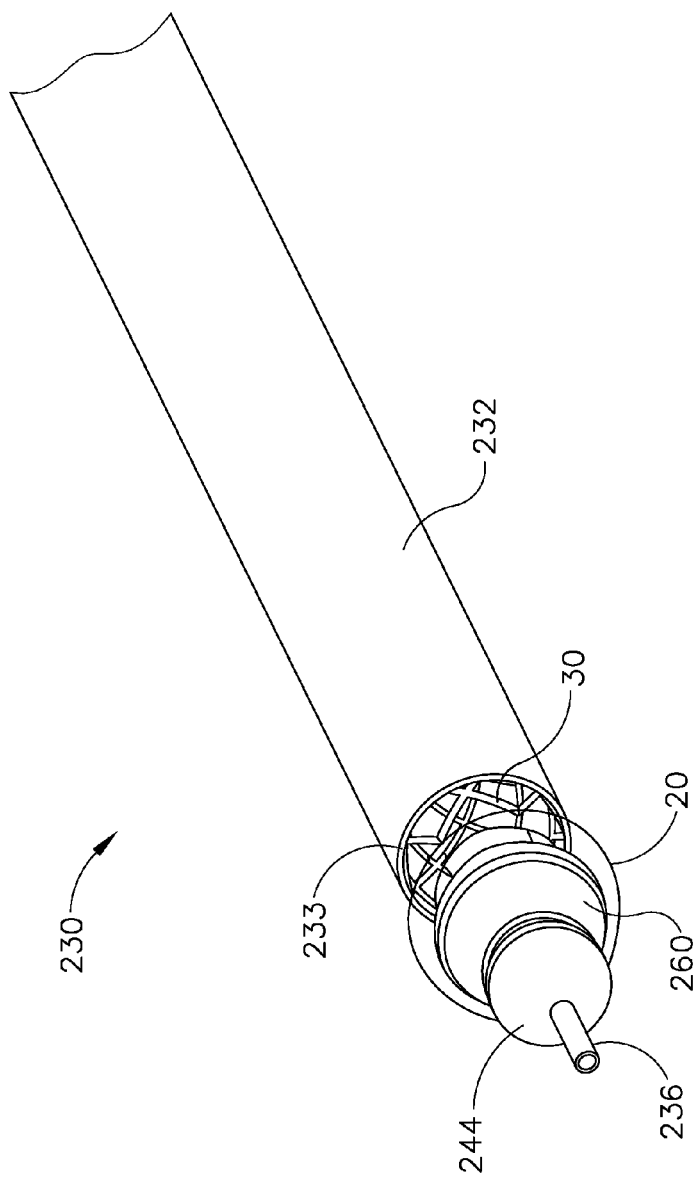
FIG. 9 depicts a partial perspective view of an exemplary alternative configuration for the distal end portion of the instrument of FIG. 3.

FIG. 9 shows the distal end of a shaft assembly (230) that may be used as a variation of shaft assembly (130). Shaft assembly (230) of this example is substantially similar to shaft assembly (130) described above, in that shaft assembly (230) includes a guidewire tube (236), a ball tip (244), and an integral tip (260). Also like shaft assembly (130) described above, shaft assembly (230) of this example is configured to carry sleeve assembly (10) at the distal end of shaft assembly (230). However, unlike shaft assembly (130) described above, shaft assembly (230) of this example includes a movable outer sheath (232). Movable outer sheath (232) is configured to transition between a distal position (shown in FIG. 9) and a proximal position. When movable outer sheath (232) is in the distal position, movable outer sheath (232) is configured to encompass anchor (50) and sealing member (30); and thereby hold anchor (50) and sealing member (30) in compressed states. When movable outer sheath (232) is in the proximal position, the distal end (233) of movable outer sheath (232) is proximal to the proximal end of anchor (50), such that movable outer sheath (232) no longer holds anchor (50) and sealing member (30) in compressed states. Movable outer sheath (232) may thus serve as a substitute for cuffs (150). Various suitable ways in which such a movable outer sheath (232) may be configured will be apparent to those of ordinary skill in the art in view of the teachings herein. Similarly, various suitable ways in which such a movable outer sheath (232) may be actuated will be apparent to those of ordinary skill in the art in view of the teachings herein.

Figure 10:
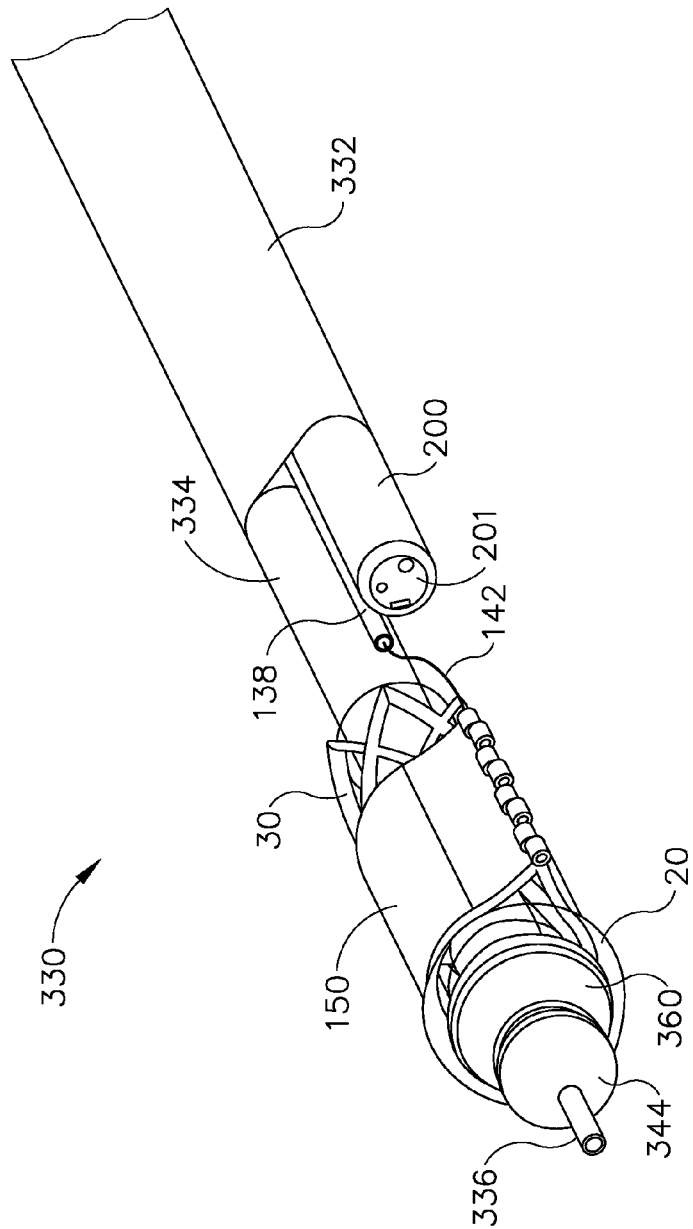
FIG. 10 depicts a partial perspective view of the distal end portion of the instrument of FIG. 3, with an endoscope secured thereto.

FIG. 10 shows the distal end of another shaft assembly (330) that may be used as a variation of shaft assembly (130). Shaft assembly (330) of this example is substantially similar to shaft assembly (130) described above, in that shaft assembly (330) includes a guidewire tube (336), a ball tip (344), an integral tip (360), an inner tubular member (334), and an offset deployment cable shaft (338). Also like shaft assembly (130) described above, shaft assembly (330) of this example is configured to carry sleeve assembly (10) at the distal end of shaft assembly (330).

However, unlike shaft assembly (130) described above, shaft assembly (330) of this example includes an outer wrap (332) that holds an endoscope (200) against inner tubular member (334) in a laterally offset fashion. Shaft assembly (330) of this example is still configured to fit down the esophagus (72), even with endoscope (200). Outer wrap (332) comprises a flexible elastomeric overtube in this example. Endoscope (200) is positioned such that the distal end (201) of endoscope (200) is just proximal to sealing member (30). Such positioning may facilitate visualization of sealing member (30) and/or other portions of instrument (100) during the process of positioning and/or deploying sleeve assembly (10). Other suitable positions for endoscope (200) in relation to shaft assembly (330) will be apparent to those of ordinary skill in the art in view of the teachings herein.

FIG. 11 shows an exemplary alternative tip member (400) that may be used as a substitute for the combination of ball tip (144) and integral tip (160). For instance, tip member (400) may be positioned at the distal end of inner tubular member (134). Tip member (400) of this example includes a plurality of distally projecting leaves (402) that are angularly separated by gaps (404). Leaves (402) taper inwardly as leaves (402) extend distally (402), and thus leaves (402) together define a generally frustoconical shape. Leaves (402) are resiliently biased to assume the positions shown in FIG. 11, yet leaves (402) may deflect inwardly when inwardly directed forces (e.g., normal forces exerted by the pylorus (64), etc.) bear upon leaves (402). Gaps (404) are configured to facilitate such inward deflection of leaves (402). It should therefore be understood that when a shaft assembly (130, 230, 330) having tip member (400) is driven distally through the pylorus (64), and the pylorus (64) presents some degree of resistance due to the size of the opening defined by the pylorus (64), leaves (402) may absorb at least some of the resistance presented by the pylorus (64) and assist in gently dilating the pylorus (64) to a state where the pylorus (64) will more freely accept the outer diameter of shaft assembly (130, 130, 330). Such dilation of the pylorus (64) may be provided by a combination of the tapered configuration of leaves (402) and the resilient bias of leaves (402). Still other suitable forms that a distal tip member may take will be apparent to those of ordinary skill in the art in view of the teachings herein.

V. Exemplary Variations of Duodenal Sleeve Assembly Anchor

As noted above, sleeve assembly (10) may be subject to various modifications. Some merely illustrative examples of such modifications are described below; while other examples will be apparent to those of ordinary skill in the art in view of the teachings herein. While the following examples relate only to variations of anchor (50), it should be understood that the various other components and features of sleeve assembly (10) may also be varied in numerous ways. Furthermore, it should be understood that anchor (50) may be varied in numerous ways other than those described below.

Figure 12:
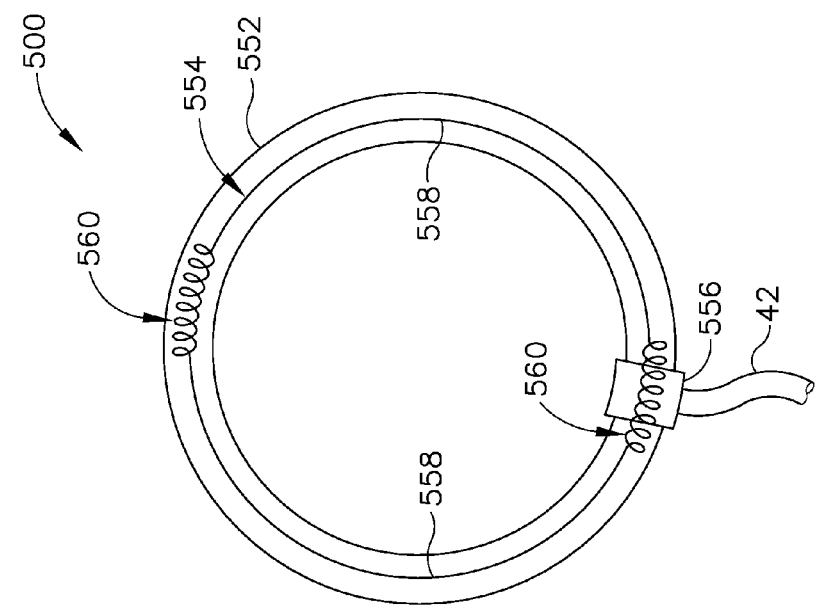
FIG. 12 depicts an exemplary alternative anchor ring for the sleeve assembly of FIG. 1.

FIG. 12 shows an exemplary alternative anchor (500) that may be used as a substitute for anchor (50) described above. Anchor (500) of the present example comprises an annular elastomeric member (552) encasing a resilient member (554). By way of example only, elastomeric member (552) may be formed of silicone and/or some other elastomeric material(s); while resilient member (554) may be formed of nitinol, spring steel, and/or some other resilient material(s). Elastomeric member (552) and resilient member (554) each define a complete ring in this example, though it should be understood that various other configurations may be used. Resilient member (554) is configured to bias anchor (500) to an expanded configuration as shown in FIG. 12, where anchor (500) has an annular shape, just like anchor (50) described above. Also like anchor (50) described above, anchor (500) of this example is coupled with tether (42) by coupling (556).

Unlike resilient member (54) of anchor (50), resilient member (554) of anchor (500) comprises a pair of coil sections (560) separating a pair of arcuate sections (558). Coil sections (560) are positioned 180° apart from each other, with one of the coil sections (560) being positioned at coupling (556). Coil sections (560) may be configured similar to torsion springs or similar to helical springs. Coil sections (560) are configured to promote flexing of anchor (500) at coil sections (560), such that coil sections (560) essentially serve as living hinges with a resilient bias. Otherwise, arcuate sections (558) are substantially identical to resilient member (54) described above. Coil sections (560) may extend along any suitable angular extent. Coil sections (560) may also be located at any other suitable angular positions in relation to coupling (556). However, it should be noted that locating a coil section (560) at the same angular position as coupling (556) may promote flexing of anchor (500) at coupling (556), which may be desirable in some instances. In some versions, coil sections (560) are formed separately from arcuate sections (558), such that sections (558, 560) are subsequently joined by welding or crimping, etc. In some other versions, coil sections (560) and arcuate sections (558) are formed from the same single continuous strip of wire or band. Other suitable ways in which resilient member (554) may be formed will be apparent to those of ordinary skill in the art in view of the teachings herein.

Figure 13:
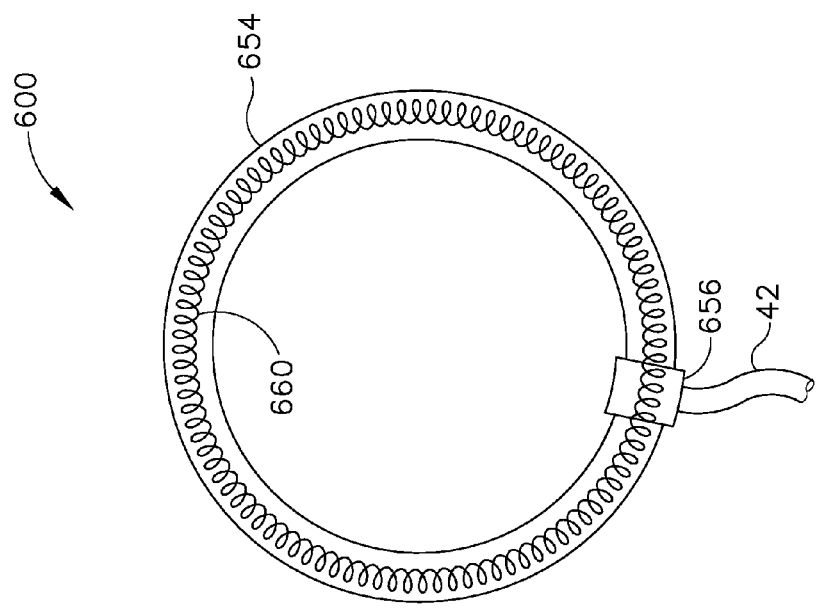
FIG. 13 depicts another exemplary alternative anchor ring for the sleeve assembly of FIG. 1.

FIG. 13 shows another exemplary alternative anchor (600) that may be used as a substitute for anchor (50) described above. Anchor (600) of the present example comprises an annular elastomeric member (652) encasing a resilient member (654). By way of example only, elastomeric member (652) may be formed of silicone and/or some other elastomeric material(s); while resilient member (654) may be formed of nitinol, spring steel, and/or some other resilient material(s). Elastomeric member (652) and resilient member (654) each define a complete ring in this example, though it should be understood that various other configurations may be used. Resilient member (654) is configured to bias anchor (600) to an expanded configuration as shown in FIG. 13, where anchor (600) has an annular shape, just like anchor (50) described above. Also like anchor (50) described above, anchor (600) of this example is coupled with tether (42) by coupling (656).

Unlike resilient member (54) of anchor (50), the entire length of resilient member (654) of anchor (600) is formed as coil. As with coil sections (560) described above, the coil forming anchor (600) may promote flexing of anchor (600). This may in turn facilitate transitioning anchor (600) to the compressed state and holding anchor (600) in the compressed state until sleeve assembly (10) is suitably positioned in the patient. Anchor (600) may nevertheless provide sufficient strength in the expanded state such that the expanded anchor (600) will not be pulled through the pylorus (64) in response to peristalsis or other distally urging forces. In some versions, anchor (600) further includes one or more stiffening elements (e.g., wire segment or tube axially oriented with resilient member (654), etc.) that provide localized stiffening in anchor (600).

FIGS. 14A-14B show another exemplary alternative anchor (700) that may be used as a substitute for anchor (50) described above. Anchor (700) of the present example comprises an annular elastomeric member (752) encasing a resilient member (754). By way of example only, elastomeric member (752) may be formed of silicone and/or some other elastomeric material(s); while resilient member (754) may be formed of nitinol, spring steel, and/or some other resilient material(s). Elastomeric member (752) defines a complete ring in this example, while resilient member (754) defines a ring segment, though it should be understood that various other configurations may be used. Resilient member (754) is configured to bias anchor (700) to an expanded configuration as shown in FIG. 14A, where anchor (700) has an annular shape, just like anchor (50) described above. Also like anchor (50) described above, anchor (700) of this example is coupled with tether (42) by coupling (756).

Unlike anchor (50), anchor (700) of the present example further defines an opening (770) that is located approximately 180° from coupling (756). Tether (42) passes through opening (770), such that tether (42) spans across the diameter of anchor (700) before exiting the outer perimeter of anchor (700). Opening (770) is sized to enable tether (42) to slide through opening (770). As shown in FIG. 14B, anchor (50) deforms by splaying outwardly when tether (42) is pulled distally through opening (770). It should be understood that this may occur after sleeve assembly (10) has been deployed in the patient. In particular, tension on tether (42) may pull anchor (700) toward the pylorus (42), and reaction loading on the pylorus (64) would cause anchor (700) to compress into the splayed configuration shown in FIG. 14B. Such a splayed configuration will increase the effective lateral width of anchor (700), thereby further preventing anchor (700) from passing through the pylorus (64). Still other suitable forms that an anchor and/or other components/features of sleeve assembly (10) may take will be apparent to those of ordinary skill in the art in view of the teachings herein.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a shaft assembly extending distally from the body;
   (c) a retention member configured to selectively expand outwardly from a closed configuration to an open configuration; and
   (d) a duodenal sleeve assembly carried by the shaft assembly, wherein the retention member in the closed configuration is configured to hold at least a portion of the duodenal sleeve assembly in a compressed state on the shaft assembly, wherein the retention member is configured to release the at least a portion of the duodenal sleeve assembly upon outward expansion of the retention member to the open configuration.

2. The apparatus of claim 1, wherein the shaft assembly has a length and outer diameter configured to permit the shaft assembly to extend from a patient's mouth to a patient's duodenum through the patient's esophagus and stomach.

3. The apparatus of claim 1, wherein the body comprises a fluid port, wherein the shaft assembly defines a lumen in fluid communication with the fluid port.

4. The apparatus of claim 3, wherein the body further comprises a user input feature operable to cause fluid from the fluid port to be communicated distally through the lumen of the shaft assembly.

5. The apparatus of claim 3, wherein the duodenal sleeve assembly comprises a sleeve, wherein a distal portion of the sleeve is positioned within the lumen of the shaft assembly.

6. The apparatus of claim 5, wherein the shaft assembly comprises a tubular member defining the lumen, wherein the tubular member has an exterior, wherein a proximal portion of the sleeve is sealed against the exterior of the tubular member.

7. The apparatus of claim 6, wherein the proximal portion of the sleeve is sealed against the exterior of the tubular member by the retention member.

8. The apparatus of claim 1, wherein the shaft assembly comprises:
   (i) an outer sheath having a distal end,
   (ii) an inner tubular member having a distal end, wherein the inner tubular member is coaxially aligned with the outer sheath, and
   (iii) a guidewire tube having a distal end, wherein the guidewire tube is coaxially aligned with the inner tubular member and outer sheath.

9. The apparatus of claim 8, wherein the shaft assembly further comprises a removable ball tip located at the distal end of the guidewire tube, wherein the distal end of the guidewire tube and the removable ball tip are distal to the distal end of the inner tubular member.

10. The apparatus of claim 8, wherein the distal end of the outer sheath terminates proximal to the distal end of the inner tubular member.

11. The apparatus of claim 1, wherein the shaft assembly includes a tapered pylorus dilation feature.

12. The apparatus of claim 1, further comprising a deployment cable, wherein the deployment cable is configured to selectively expand the retention member from the closed configuration to the open configuration and release the retention member from the duodenal sleeve assembly.

13. The apparatus of claim 12, wherein the body comprises a user input feature operable to selectively retract the deployment cable to thereby release the retention member from the duodenal sleeve assembly.

14. The apparatus of claim 1, wherein the retention member comprises a cuff.

15. The apparatus of claim 14, wherein the cuff is resiliently biased to assume an expanded configuration, wherein the cuff is configured to hold at least a portion of the duodenal sleeve assembly in a compressed state on the shaft assembly when the cuff is in a compressed state.

16. The apparatus of claim 1, wherein the duodenal sleeve assembly comprises:
   (i) a sleeve,
   (ii) an expandable sealing member coupled with the sleeve, (iii) a tether coupled with the sealing member, and
(iv) an expandable anchor coupled with the tether.

17. The apparatus of claim 16, wherein the retention member is configured to selectively hold the sealing member in a compressed state on the shaft assembly.

18. The apparatus of claim 17, further comprising a second retention member configured to selectively hold the anchor in a compressed state on the shaft assembly.

19. An apparatus comprising:
(a) a body;
(b) a shaft assembly extending distally from the body, wherein the shaft assembly comprises an inner lumen and an exterior surface;
(c) a duodenal sleeve assembly, comprising:
  (i) a sleeve, wherein at least a portion of the sleeve is disposed in the inner lumen of the shaft assembly,
  (ii) an expandable sealing member coupled with the sleeve, and
  (iii) an expandable anchor coupled with the sealing member;
(d) a first retention member selectively securing the sealing member to the exterior surface of the shaft assembly; and
(e) a second retention member selectively securing the anchor to the exterior surface of the shaft assembly.

20. A method of using an instrument to deploy a duodenal sleeve assembly, wherein the duodenal sleeve assembly comprises a sleeve, an expandable sealing member, a tether, and an expandable anchor, wherein the sleeve is secured to the sealing member, wherein the tether couples the anchor with the sealing member, wherein the instrument comprises a shaft assembly, a first retention member, and a second retention member, wherein the first retention member selectively secures the sealing member to the shaft assembly, wherein the second retention member selectively secures the anchor to the shaft assembly, the method comprising:
(a) inserting the shaft assembly transorally through a patient's esophagus and stomach such that a distal end of the shaft assembly is positioned in the patient's duodenum, wherein a portion of the sleeve is disposed within the shaft assembly during the act of inserting;
(b) unfurling the portion of the sleeve from the shaft assembly such that the sleeve lines the interior of the duodenum;
(c) releasing the first retention member to release the sealing member from the shaft assembly, wherein the released sealing member seals a proximal end of the sleeve against the mucosa of the duodenum; and
(d) releasing the second retention member to release the anchor from the shaft assembly, wherein the anchor is released within the stomach, wherein the tether traverses the pylorus.

* * * * *